(12) United States Patent
Free et al.

(10) Patent No.: US 11,857,207 B2
(45) Date of Patent: *Jan. 2, 2024

(54) CIRCULAR FIXATOR SYSTEM AND METHOD

(71) Applicant: WRIGHT MEDICAL TECHNOLOGY, INC., Memphis, TN (US)

(72) Inventors: Daniel E. Free, Arlington, TN (US); Robert M. Howles, Bartlett, TN (US); Elizabeth J. Phelps, Collierville, TN (US); Kian-Ming Wong, Lakeland, TN (US); Braham Dhillon, Memphis, TN (US)

(73) Assignee: WRIGHT MEDICAL TECHNOLOGY, INC., Memphis, TN (US)

(*) Notice: Subject to any disclaimer, the term of this patent is extended or adjusted under 35 U.S.C. 154(b) by 0 days.

This patent is subject to a terminal disclaimer.

(21) Appl. No.: 18/056,027

(22) Filed: Nov. 16, 2022

(65) Prior Publication Data
US 2023/0070584 A1 Mar. 9, 2023

Related U.S. Application Data

(62) Division of application No. 17/079,852, filed on Oct. 26, 2020, now Pat. No. 11,529,152, which is a
(Continued)

(51) Int. Cl.
*A61B 17/17* (2006.01)
*A61B 17/64* (2006.01)
(Continued)

(52) U.S. Cl.
CPC ...... *A61B 17/1775* (2016.11); *A61B 17/1642* (2013.01); *A61B 17/1682* (2013.01);
(Continued)

(58) Field of Classification Search
CPC ... A61B 17/1775; A61B 17/15; A61B 17/157; A61B 17/6452; A61B 17/171;
(Continued)

(56) References Cited

U.S. PATENT DOCUMENTS 3,839,742 A 10/1974 Link
3,872,519 A 3/1975 Giannestras et al.
(Continued)

FOREIGN PATENT DOCUMENTS

CA 2836651 3/2016
CN 101790353 7/2010
(Continued)

OTHER PUBLICATIONS

Search report issued for European patent application No. 13198280 dated Feb. 5, 2014.
(Continued)

*Primary Examiner* — Marcela I. Shirsat
(74) *Attorney, Agent, or Firm* — DUANE MORRIS LLP

(57) ABSTRACT

A device comprises a base. A support is attached to the base. The support is shaped to receive a calf of a person and adapted to receive a wire or pin for securing a tibia of a person. A foot plate is attachable to the base. The foot plate has a plurality of attached members. The members are configured for receiving at least a first wire or pin to fix a foot of the person relative to the foot plate while the foot plate is oriented normal to a superior-inferior direction of the foot. The foot plate is rotatable relative to the base while the foot plate is attached to the base.

16 Claims, 34 Drawing Sheets

Related U.S. Application Data division of application No. 16/072,043, filed as application No. PCT/US2016/023729 on Mar. 23, 2016, now Pat. No. 11,134,964.

(51) Int. Cl.

| | | |
|---|---|---|
| *A61G 13/12* | (2006.01) | |
| *A61F 2/42* | (2006.01) | |
| *A61B 17/15* | (2006.01) | |
| *A61F 2/46* | (2006.01) | |
| *A61B 17/16* | (2006.01) | |
| *A61B 90/00* | (2016.01) | |

(52) U.S. Cl.
CPC ........ *A61B 17/6425* (2013.01); *A61G 13/125* (2013.01); *A61B 17/157* (2013.01); *A61B 17/1659* (2013.01); *A61B 17/171* (2013.01); *A61B 17/1739* (2013.01); *A61B 2090/034* (2016.02); *A61F 2/4202* (2013.01); *A61F 2/4606* (2013.01); *A61F 2002/4205* (2013.01); *A61F 2002/4207* (2013.01); *A61G 13/129* (2013.01); *A61G 13/1295* (2013.01)

(58) Field of Classification Search
CPC ........... A61B 17/1739; A61B 2017/564; A61F 2002/4205; A61F 2002/4207; A61F 2/4202; A61F 2/42; A61G 13/125; A61G 13/129; A61G 13/2395
USPC .......... 606/87–88, 96–98, 103–104
See application file for complete search history.

(56) References Cited

U.S. PATENT DOCUMENTS

| | | |
|---|---|---|
| 3,886,599 A | 6/1975 | Schlein |
| 3,889,300 A | 6/1975 | Smith |
| 3,896,502 A | 7/1975 | Lennox |
| 3,896,503 A | 7/1975 | Freeman et al. |
| 3,975,778 A | 8/1976 | Newton, III |
| 3,987,500 A | 10/1976 | Schlein |
| 4,021,864 A | 5/1977 | Waugh |
| 4,069,518 A | 1/1978 | Groth, Jr. et al. |
| 4,156,944 A | 6/1979 | Schreiber et al. |
| 4,166,292 A | 9/1979 | Bokros |
| 4,204,284 A | 5/1980 | Koeneman |
| 4,232,404 A | 11/1980 | Samuelson et al. |
| 4,309,778 A | 1/1982 | Buechel et al. |
| 4,470,158 A | 9/1984 | Pappas et al. |
| 4,755,185 A | 7/1988 | Tarr |
| 4,968,316 A | 11/1990 | Hergenroeder |
| 5,041,139 A | 8/1991 | Brånemark |
| 5,312,412 A | 5/1994 | Whipple |
| 5,326,365 A | 7/1994 | Alvine |
| 5,354,300 A | 10/1994 | Goble et al. |
| 5,423,825 A | 6/1995 | Levine |
| 5,476,466 A | 12/1995 | Barrette et al. |
| 5,601,563 A | 2/1997 | Burke et al. |
| 5,628,749 A | 5/1997 | Vendrely et al. |
| 5,634,927 A | 6/1997 | Houston et al. |
| 5,667,511 A | 9/1997 | Vendrely et al. |
| 5,674,223 A | 10/1997 | Cipolletti et al. |
| 5,735,904 A | 4/1998 | Pappas |
| 5,766,259 A | 6/1998 | Sammarco |
| 5,776,200 A | 7/1998 | Johnson et al. |
| 5,817,097 A | 10/1998 | Howard et al. |
| 5,824,106 A | 10/1998 | Fournal |
| 5,879,389 A | 3/1999 | Koshino |
| 5,885,299 A | 3/1999 | Winslow et al. |
| 5,888,203 A | 3/1999 | Goldberg |
| 5,897,559 A | 4/1999 | Masini |
| 5,910,143 A * | 6/1999 | Cripe ................ A61B 17/1764 606/88 |
| 5,935,132 A | 8/1999 | Bettuchi et al. |
| 6,002,859 A | 12/1999 | DiGioia, III et al. |
| 6,033,405 A | 3/2000 | Winslow et al. |
| 6,102,952 A | 8/2000 | Koshino |
| 6,183,519 B1 | 2/2001 | Bonnin et al. |
| 6,245,109 B1 | 6/2001 | Mendes et al. |
| 6,342,056 B1 | 1/2002 | Mac-Thiong et al. |
| 6,344,043 B1 | 2/2002 | Pappas |
| 6,409,767 B1 | 6/2002 | Pericé et al. |
| 6,436,146 B1 | 8/2002 | Hassler et al. |
| 6,478,800 B1 | 11/2002 | Fraser et al. |
| 6,520,964 B2 | 2/2003 | Tallarida et al. |
| 6,530,930 B1 | 3/2003 | Marino et al. |
| 6,602,259 B1 | 8/2003 | Masini |
| 6,610,067 B2 | 8/2003 | Tallarida et al. |
| 6,610,095 B1 | 8/2003 | Pope et al. |
| 6,620,168 B1 | 9/2003 | Lombardo et al. |
| 6,645,215 B1 | 11/2003 | McGovern et al. |
| 6,663,669 B1 | 12/2003 | Reiley |
| 6,673,116 B2 | 1/2004 | Reiley |
| 6,679,917 B2 | 1/2004 | Ek |
| 6,719,799 B1 | 4/2004 | Kropf |
| 6,824,567 B2 | 11/2004 | Tornier et al. |
| 6,852,130 B2 | 2/2005 | Keller et al. |
| 6,860,902 B2 | 3/2005 | Reiley |
| 6,863,691 B2 | 3/2005 | Short et al. |
| 6,875,222 B2 | 4/2005 | Long et al. |
| 6,875,236 B2 | 4/2005 | Reiley |
| 6,926,739 B1 | 8/2005 | O'Connor et al. |
| 6,939,380 B2 | 9/2005 | Guzman |
| 6,942,670 B2 | 9/2005 | Heldreth et al. |
| 6,964,663 B2 | 11/2005 | Grant et al. |
| 7,001,394 B2 | 2/2006 | Gundlapalli et al. |
| 7,011,687 B2 | 3/2006 | Deffenbaugh et al. |
| 7,025,790 B2 | 4/2006 | Parks et al. |
| 7,163,541 B2 | 1/2007 | Ek |
| 7,238,190 B2 | 7/2007 | Schon et al. |
| 7,252,684 B2 | 8/2007 | Dearnaley |
| 7,314,488 B2 | 1/2008 | Reiley |
| 7,323,012 B1 | 1/2008 | Stone et al. |
| 7,476,227 B2 | 1/2009 | Tornier et al. |
| 7,481,814 B1 | 1/2009 | Metzger |
| 7,485,147 B2 | 2/2009 | Papps et al. |
| 7,534,246 B2 | 5/2009 | Reiley et al. |
| 7,534,270 B2 | 5/2009 | Ball |
| 7,615,082 B2 | 11/2009 | Naegerl et al. |
| 7,618,421 B2 | 11/2009 | Axelson, Jr. et al. |
| 7,625,409 B2 | 12/2009 | Saltzman et al. |
| 7,641,697 B2 | 1/2010 | Reiley |
| 7,678,151 B2 | 3/2010 | Ek |
| 7,713,305 B2 | 5/2010 | Ek |
| 7,717,920 B2 | 5/2010 | Reiley |
| 7,763,080 B2 | 7/2010 | Southworth |
| 7,803,158 B2 | 9/2010 | Hayden |
| 7,850,698 B2 | 12/2010 | Straszheim-Morley et al. |
| 7,896,883 B2 | 3/2011 | Ek et al. |
| 7,896,885 B2 | 3/2011 | Miniaci et al. |
| 7,909,882 B2 | 3/2011 | Stinnette |
| 7,914,533 B2 | 3/2011 | Nelson et al. |
| 7,963,996 B2 | 6/2011 | Saltzman et al. |
| 8,002,841 B2 | 8/2011 | Hasselman |
| 8,012,217 B2 | 9/2011 | Strzepa et al. |
| 8,034,114 B2 | 10/2011 | Reiley |
| 8,034,115 B2 | 10/2011 | Reiley |
| 8,048,164 B2 | 11/2011 | Reiley |
| 8,110,006 B2 | 2/2012 | Reiley |
| 8,114,091 B2 | 2/2012 | Ratron et al. |
| 8,128,627 B2 | 3/2012 | Justin et al. |
| 8,167,888 B2 | 5/2012 | Steffensmeier |
| 8,172,850 B2 | 5/2012 | McMinn |
| 8,177,841 B2 | 5/2012 | Ek |
| 8,192,434 B2 | 6/2012 | Huebner et al. |
| 8,268,007 B2 | 9/2012 | Barsoum et al. |
| 8,303,667 B2 | 11/2012 | Younger |
| 8,313,492 B2 | 11/2012 | Wong et al. |
| 8,317,797 B2 | 11/2012 | Rasmussen |
| 8,323,346 B2 | 12/2012 | Tepic |
| 8,337,503 B2 | 12/2012 | Lian |
| 8,361,159 B2 | 1/2013 | Ek |
| 8,430,879 B2 | 4/2013 | Stoneburner et al. |

(56) References Cited

U.S. PATENT DOCUMENTS

| | | |
|---|---|---|
| 8,475,463 B2 | 7/2013 | Lian |
| 8,491,596 B2 | 7/2013 | Long et al. |
| 8,579,980 B2 | 11/2013 | DeLurio et al. |
| 8,636,744 B2 * | 1/2014 | Tochigi ............... A61F 2/4202 606/87 |
| 8,715,362 B2 | 5/2014 | Reiley et al. |
| 8,808,303 B2 | 8/2014 | Stemniski et al. |
| 8,911,444 B2 | 12/2014 | Bailey |
| 9,259,250 B2 | 2/2016 | Saravia et al. |
| 9,480,571 B2 | 11/2016 | McGinley et al. |
| 9,492,281 B2 | 11/2016 | Rouyer et al. |
| 9,629,726 B2 | 4/2017 | Reiley et al. |
| 9,629,730 B2 | 4/2017 | Reiley |
| 9,907,561 B2 | 3/2018 | Luna et al. |
| 10,034,678 B2 | 7/2018 | Park et al. |
| 10,039,558 B2 | 8/2018 | Park et al. |
| 10,136,904 B2 | 11/2018 | McGinley et al. |
| 10,149,687 B2 | 12/2018 | McGinley et al. |
| 10,182,832 B1 | 1/2019 | Saltzman et al. |
| 10,206,688 B2 | 2/2019 | Park et al. |
| 10,743,999 B2 | 8/2020 | Reiley |
| 10,940,012 B2 | 3/2021 | Sander et al. |
| 11,134,964 B2 * | 10/2021 | Free ................... A61B 17/6425 |
| 2002/0068977 A1 | 6/2002 | Jackson |
| 2002/0082607 A1 | 6/2002 | Heldreth et al. |
| 2002/0133164 A1 | 9/2002 | Williamson |
| 2002/0173853 A1 | 11/2002 | Corl, III et al. |
| 2003/0208280 A1 | 11/2003 | Tohidi |
| 2003/0236522 A1 | 12/2003 | Long et al. |
| 2004/0030399 A1 | 2/2004 | Asencio |
| 2004/0039394 A1 | 2/2004 | Conti et al. |
| 2004/0068322 A1 | 4/2004 | Ferree |
| 2004/0167631 A1 | 8/2004 | Luchesi et al. |
| 2004/0186585 A1 | 9/2004 | Feiwell |
| 2004/0193268 A1 | 9/2004 | Hazebrouck |
| 2004/0216259 A1 | 11/2004 | Ponziani |
| 2004/0236431 A1 | 11/2004 | Sekel |
| 2005/0004676 A1 | 1/2005 | Schon et al. |
| 2005/0165408 A1 | 7/2005 | Puno et al. |
| 2005/0192674 A1 | 9/2005 | Ferree |
| 2006/0009857 A1 | 1/2006 | Gibbs et al. |
| 2006/0020345 A1 | 1/2006 | O'Connor et al. |
| 2006/0036257 A1 | 2/2006 | Steffensmeier |
| 2006/0116679 A1 | 6/2006 | Lutz et al. |
| 2006/0142870 A1 | 6/2006 | Robinson et al. |
| 2006/0229730 A1 | 10/2006 | Railey et al. |
| 2006/0235541 A1 | 10/2006 | Hodorek |
| 2006/0247788 A1 | 11/2006 | Ross |
| 2007/0038303 A1 | 2/2007 | Myerson et al. |
| 2007/0100346 A1 | 5/2007 | Wyss et al. |
| 2007/0112431 A1 | 5/2007 | Kofoed |
| 2007/0162025 A1 | 7/2007 | Tornier et al. |
| 2007/0173944 A1 | 7/2007 | Keller et al. |
| 2007/0173947 A1 | 7/2007 | Ratron et al. |
| 2007/0213830 A1 | 9/2007 | Ammann et al. |
| 2007/0233129 A1 | 10/2007 | Bertagnoli et al. |
| 2007/0276400 A1 | 11/2007 | Moore et al. |
| 2007/0288030 A1 | 12/2007 | Metzger et al. |
| 2008/0015602 A1 | 1/2008 | Axelson |
| 2008/0097617 A1 | 4/2008 | Fellinger et al. |
| 2008/0103603 A1 | 5/2008 | Hintermann |
| 2008/0109081 A1 | 5/2008 | Bao et al. |
| 2008/0195233 A1 | 8/2008 | Ferrari et al. |
| 2008/0215156 A1 | 9/2008 | Duggal et al. |
| 2008/0287954 A1 | 11/2008 | Kunz et al. |
| 2008/0312745 A1 | 12/2008 | Keller et al. |
| 2009/0024131 A1 | 1/2009 | Metzger et al. |
| 2009/0043309 A1 | 2/2009 | Rasmussen |
| 2009/0043310 A1 | 2/2009 | Rasmussen |
| 2009/0054992 A1 | 2/2009 | Landes et al. |
| 2009/0082875 A1 | 3/2009 | Long |
| 2009/0105767 A1 | 4/2009 | Reiley |
| 2009/0105840 A1 | 4/2009 | Reiley |
| 2009/0182433 A1 | 7/2009 | Reiley et al. |
| 2009/0198341 A1 | 8/2009 | Choi et al. |
| 2009/0234360 A1 | 9/2009 | Alexander |
| 2009/0276052 A1 | 11/2009 | Regala et al. |
| 2010/0010493 A1 | 1/2010 | Dower |
| 2010/0023066 A1 | 1/2010 | Long et al. |
| 2010/0023126 A1 | 1/2010 | Grotz |
| 2010/0057216 A1 | 3/2010 | Gannoe et al. |
| 2010/0069910 A1 | 3/2010 | Hasselman |
| 2010/0198355 A1 | 8/2010 | Kofoed et al. |
| 2010/0212138 A1 | 8/2010 | Carroll et al. |
| 2010/0241237 A1 | 9/2010 | Pappas |
| 2010/0262150 A1 | 10/2010 | Lian |
| 2010/0305572 A1 | 12/2010 | Saltzman et al. |
| 2010/0318088 A1 | 12/2010 | Warne et al. |
| 2010/0331984 A1 | 12/2010 | Barsoum et al. |
| 2011/0029090 A1 | 2/2011 | Zannis et al. |
| 2011/0035018 A1 | 2/2011 | Deffenbaugh et al. |
| 2011/0035019 A1 | 2/2011 | Goswami et al. |
| 2011/0071645 A1 | 3/2011 | Bojarski et al. |
| 2011/0106268 A1 | 5/2011 | Deffenbaugh et al. |
| 2011/0112542 A1 | 5/2011 | Gross |
| 2011/0125200 A1 | 5/2011 | Hanson et al. |
| 2011/0125275 A1 | 5/2011 | Lipman et al. |
| 2011/0125284 A1 | 5/2011 | Gabbrielli et al. |
| 2011/0152868 A1 | 6/2011 | Kourtis et al. |
| 2011/0152869 A1 | 6/2011 | Ek et al. |
| 2011/0166608 A1 | 7/2011 | Duggal et al. |
| 2011/0190829 A1 | 8/2011 | Duggal et al. |
| 2011/0218542 A1 | 9/2011 | Lian |
| 2011/0245835 A1 | 10/2011 | Dodds et al. |
| 2011/0253151 A1 | 10/2011 | Tochigi et al. |
| 2011/0276052 A1 | 11/2011 | Hasselman |
| 2011/0295380 A1 | 12/2011 | Long |
| 2012/0010718 A1 | 1/2012 | Still |
| 2012/0046753 A1 | 2/2012 | Cook et al. |
| 2012/0053591 A1 | 3/2012 | Haines et al. |
| 2012/0053644 A1 | 3/2012 | Landry et al. |
| 2012/0083789 A1 | 4/2012 | Blakemore et al. |
| 2012/0109131 A1 | 5/2012 | Vasarhelyi et al. |
| 2012/0109326 A1 | 5/2012 | Perler |
| 2012/0130376 A1 | 5/2012 | Loring et al. |
| 2012/0136443 A1 | 5/2012 | Wenzel |
| 2012/0185057 A1 | 7/2012 | Abidi et al. |
| 2012/0191210 A1 | 7/2012 | Ratron et al. |
| 2012/0239045 A1 | 9/2012 | Li |
| 2012/0245701 A1 | 9/2012 | Zak et al. |
| 2012/0271314 A1 | 10/2012 | Stemniski et al. |
| 2012/0271430 A1 | 10/2012 | Arnett et al. |
| 2012/0277745 A1 | 11/2012 | Lizee |
| 2013/0041473 A1 | 2/2013 | Rouyer et al. |
| 2013/0116797 A1 | 5/2013 | Coulange et al. |
| 2014/0020690 A1 * | 1/2014 | Triplett ............... A61G 13/128 128/845 |
| 2014/0236157 A1 | 8/2014 | Tochigi et al. |
| 2014/0276853 A1 | 9/2014 | Long et al. |
| 2014/0296995 A1 | 10/2014 | Reiley et al. |
| 2014/0309640 A1 | 10/2014 | Smith et al. |
| 2014/0336658 A1 | 11/2014 | Luna et al. |
| 2015/0045801 A1 | 2/2015 | Axelson, Jr. et al. |
| 2016/0135815 A1 | 5/2016 | Loring et al. |
| 2017/0224383 A1 * | 8/2017 | Wong ................ A61B 17/6458 |
| 2018/0177511 A1 | 6/2018 | Luna et al. |
| 2018/0263639 A1 | 9/2018 | McGinley et al. |
| 2019/0059917 A1 | 2/2019 | Saltzman |
| 2019/0059918 A1 | 2/2019 | Saltzman et al. |
| 2019/0133612 A1 | 5/2019 | McGinley et al. |

FOREIGN PATENT DOCUMENTS

| | | |
|---|---|---|
| EP | 2967697 | 4/2018 |
| EP | 3354233 | 10/2019 |
| GB | 2480846 | 12/2011 |
| JP | H11-500035 | 1/1999 |
| JP | 2006150055 | 6/2006 |
| JP | 2007508123 | 4/2007 |
| JP | 2007518453 | 7/2007 |
| JP | 2007519477 | 7/2007 |
| JP | 2007536011 | 12/2007 |
| JP | 2009148597 | 7/2009 |
| JP | 2011526189 | 10/2011 |

(56) References Cited

FOREIGN PATENT DOCUMENTS

| | | |
|---|---|---|
| JP | 2012518517 | 8/2012 |
| JP | 2013500810 | 1/2013 |
| JP | 2013511358 | 4/2013 |
| JP | 5412334 | 2/2014 |
| JP | 2014131738 | 7/2014 |
| WO | WO 9625106 | 8/1996 |
| WO | WO 0166021 A1 | 9/2001 |
| WO | WO 2005011523 A2 | 2/2005 |
| WO | WO 2005037135 | 4/2005 |
| WO | WO 2006022923 | 3/2006 |
| WO | WO 2006023824 | 3/2006 |
| WO | WO 2006099270 | 9/2006 |
| WO | WO 2007084846 | 7/2007 |
| WO | WO 2009143374 | 11/2009 |
| WO | WO 2009158522 | 12/2009 |
| WO | WO 2010099142 | 9/2010 |
| WO | WO 2010135156 | 11/2010 |
| WO | WO 2011015863 | 2/2011 |
| WO | WO 2011063281 | 5/2011 |
| WO | WO 2011151657 | 12/2011 |
| WO | WO 2012088036 | 6/2012 |
| WO | WO 2012116089 | 8/2012 |
| WO | WO 2012158917 | 11/2012 |
| WO | WO 2013169475 | 11/2013 |
| WO | WO 2014152535 | 9/2014 |
| WO | WO 2015167581 | 11/2015 |
| WO | WO 2016005722 | 1/2016 |
| WO | WO 2016039762 | 3/2016 |

OTHER PUBLICATIONS

International Search Report for International patent application No. PCT/US2014/027448 dated Jul. 7, 2014.
International Preliminary Report on Patentability issued for International patent application No. PCT/US2014/027448, dated Sep. 15, 2015, 8 pages.
Partial European Search Report issued in connection with European patent application No. 147683338, datea Oct. 26, 2016, 6 pages.
Patent Examination Report No. 1 issued in connection with Australian patent application No. 2015202080, dated Jul. 5, 2016, 4 pages.
First Office Action issued for Japanese patent application No. 2016-117842, dated Sep. 12, 2017, 5 pages.
First Office Action issued in connection with corresponding Japanese Patent Application No. 2020-016447, dated Apr. 6, 2021, 4 pages.
Office Action in corresponding Canadian Patent Application No. 2,904,652, dated Jun. 2, 2020, 6 pages.
First Examination Report issued in corresponding Australian Patent Application No. 2019213412, dated Sep. 3, 2020, 5 pages.
First Office Action in corresponding Canadian Patent Application No. 2,904,652, dated Jan. 28, 2020, 5 pages.
Final Office Action issued in connection with corresponding Japanese Patent Application No. 206-502443, dated May 15, 2018, 3 pages.
Extended European Search Report issued in connection with corresponding European Patent Application No. 181603788, dated Jun. 29,2018, 7 pages.
Second Office Action issued in connection with corresponding Chinese Patent Application No. 2018071101785100, dated Jul. 16, 2016, 6 pages.
First Office Action in corresponding Japanese Patent Application No. 2018-178853, dated Sep. 3,2018, 3 pages.
Examination Report No. 1 issued in connection with corresponding Australian Patent Application No. 20182000073, dated Dec. 24, 2018, 3 pages.
First Office Action issued in connection with corresponding Japanese Patent Application No. 2018-092289, dated Mar. 5, 2019, 2 pages.
Extended European Search Report and Opinion in connection with European Patent Application No. 147683338, dated Jan. 30,2017, 10 pages.
First Office Action issued in connection with Chinese Patent Application No. 2017800899442 dated Apr. 6, 2022, 8 pages.
International Search Report and Written Opinion issued in connection with International Patent Application No. PCT/US2021/025873, dated Sep. 2, 2021.
Orthopedic Designs North America, Inc., http://odi-na.com/?service=talon-distalfix-fermoral-nail-system, accessed via Internet, Jul. 22, 2022.
Arthrex, "Arthrex—Intramedullary Nails," https://ww.arthrex.com/foot-ankle/intramedullary-nails, accessed via Internet, Jul. 22, 2022.
Inbone II Total Ankle Surgical Technique, Wright Medical Technology, Inc., Mar. 12, 2014, 64 pages.
Infinity Total Ankle System Surgical Technique, Wright Medical Techology, Inc., Aug. 8, 2015, 76 pages.
First Examination Report issued in connection with Australian Patent Application No. 2020277219, dated Nov. 19, 2021, 7 pages.
International Search Report and Written Opinion issued in connection with International Patent Application No. PCT/US2016/023729, dated Feb. 14, 2017, 14 pages.
First Examination Report issued in connection with Australian Patent Application No. 2019246766, dated Apr. 17, 2020, 9 pages.
Supplementary European Search Report issued in connection with corresponding European Patent Application No. 16895669.6 dated Oct. 21, 2019, 6 pages.
Office Action in connection with corresponding Canadian Patent Application No. 3,014,284, dated Jun. 17, 2019, 4 pages.
First Examination issued in connection with Australian Patent Application No. 2016398429, dated Jan. 21, 2019, 4 pages.

\* cited by examiner

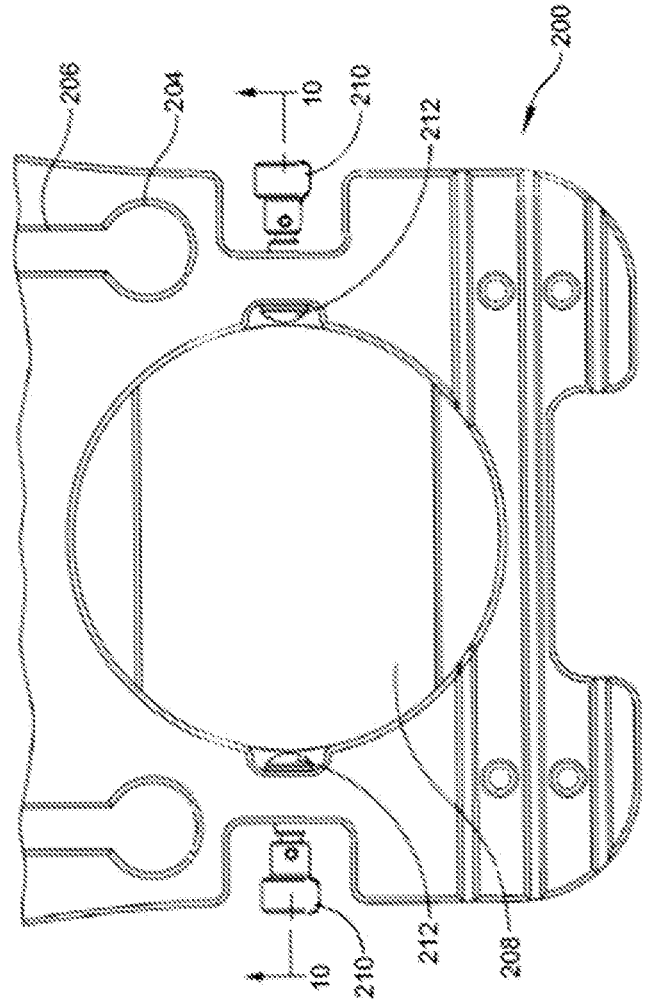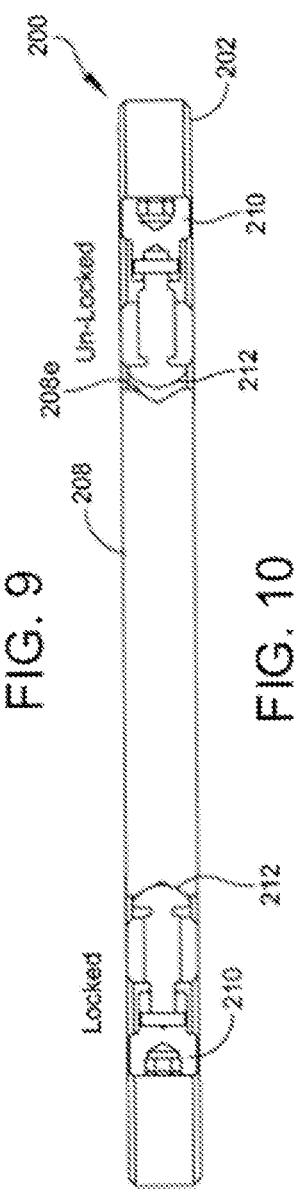
FIG. 9
FIG. 10

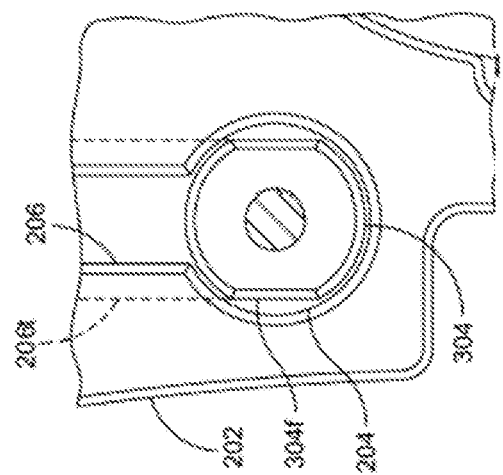
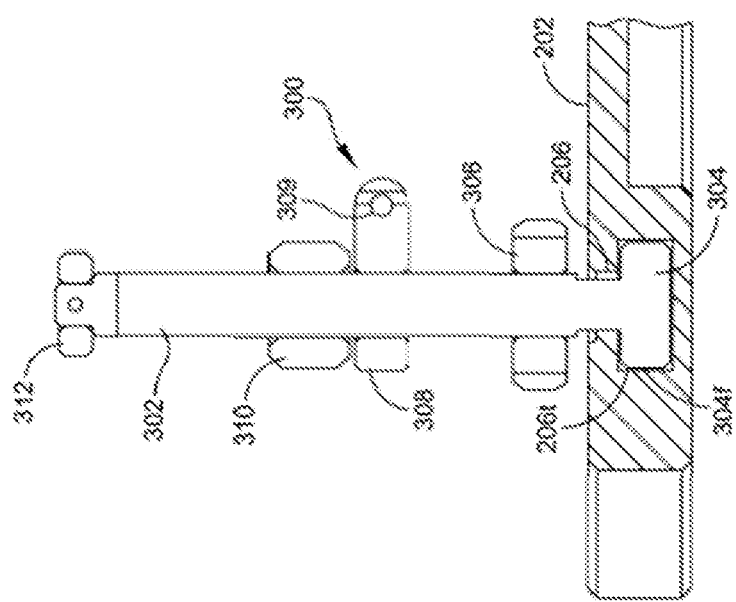

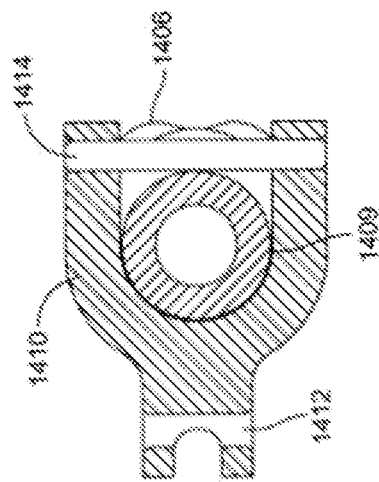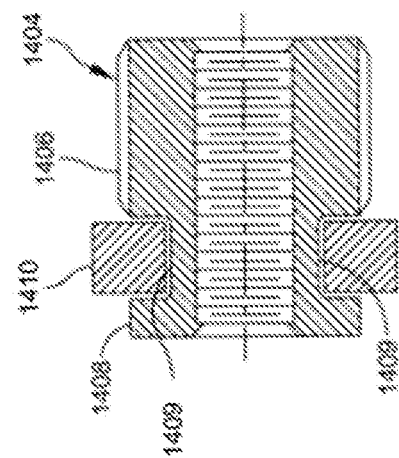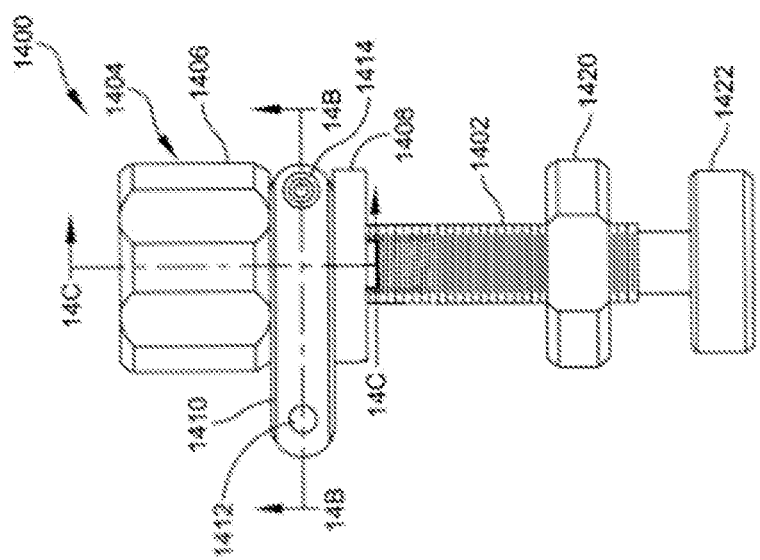

CIRCULAR FIXATOR SYSTEM AND METHOD

CROSS-REFERENCE TO RELATED APPLICATIONS

This application is a divisional of U.S. patent application Ser. No. 17/079,852, filed Oct. 26, 2020, which is a divisional of U.S. patent application No. 16/072,043, filed Jul. 23, 2018 (now U.S. Pat. No. 11,134,964), which is a national phase entry under 35 U.S.C. § 371 of International Patent Application No. PCT/US2016/023729, filed Mar. 23, 2016, which are expressly incorporated herein by reference in its entireties.

FIELD

This disclosure relates to orthopedic implants.

BACKGROUND

An ankle joint may become severely damaged and painful due to arthritis from prior ankle surgery, bone fracture, infection, osteoarthritis, posttraumatic osteoarthritis or rheumatoid arthritis, for example. Options for treating the injured ankle have included anti-inflammatory and pain medications, braces, physical therapy, amputation, joint arthrodesis, and total ankle replacement.

Total angle replacement is a complex surgical procedure. The "INVISON®" Total Ankle Revision System by Wright Medical Technology, Inc. of Memphis, Tenn. offers a surgical technique for facilitating ankle prosthesis surgery.

SUMMARY

In some embodiments, a device, comprises a base. A foot plate is attached to the base. The foot plate has a plurality of members attached thereto. The members are configured for receiving at least a first wire or pin to fix a foot of a person relative to the foot plate while the foot plate is oriented normal to a superior-inferior direction of the foot. An assembly is attached to the base. The assembly includes a support shaped to receive a calf of a person, and a positioning assembly for attaching the support to the base, including a first mechanism for positioning the support in a superior-inferior direction relative to the base.

In some embodiments, a device, comprises a base. A support is attached to the base. In some embodiments, the support is a tray is shaped to receive a calf of a person and adapted to receive a wire or pin for securing a tibia of a person. A foot plate is attachable to the base. The foot plate has a plurality of members attached thereto. The members are configured for receiving at least a first wire or pin to fix a foot of the person relative to the foot plate while the foot plate is oriented normal to a superior-inferior direction of the foot. The foot plate is rotatable relative to the base while the foot plate is attached to the base.

In some embodiments, a method comprises: cutting a talus of a person along a transverse plane to form a cut surface of the talus, wherein the talus has a void in the cut surface, the void having a size and a location; fitting a talar component to the cut surface of the talus; inserting a plurality of wires or pins through the talar component into the talus; removing the talar component; sliding a reamer base over the plurality of wires or pins into a position on the talus, the reamer base having an arm; attaching a reamer to the arm, the reamer having a size corresponding to the size of the void, the reamer having a stop; and rotating the reamer to ream the cut surface at the location of the void, until the stop engages the arm, so the reamer moves a predetermined distance while reaming the cut surface, to enlarge the void to receive an augment component having a predetermined size and shape.

In some embodiments, a method comprises: fixing a talus of a patient to a foot holder; aligning the talus with a tibia of the patient; attaching a cartridge holder to the foot holder; and attaching a resection guide or a sizing guide to the cartridge holder, the cartridge holder and the resection guide or sizing guide configured so that, when the resection guide or sizing guide is attached, the resection guide is positioned and aligned to cut the talus and tibia, or the sizing guide is positioned and aligned to drill holes in the talus and tibia, respectively.

BRIEF DESCRIPTION OF THE DRAWINGS

FIG. 9 is an enlarged detail of FIG. 8.

FIG. 10 is a cross-sectional view of the foot plate of FIG. 9, taken along section line 10-10 of FIG. 9.

FIG. 13A is a cross-sectional view of the compression member of FIG. 12, taken along section line 13A-13A of FIG. 12.

FIG. 13B shows a detail of the alignment between the compression member and foot plate of FIG. 12.

FIGS. 14A-14C show a variation of the compression member of FIGS. 13A-13B. FIG. 14B is a cross sectional view taken along section line 14B-14B of FIG. 14A. FIG. 14C is a cross sectional view taken along section line 14C-14C of FIG. 14A.

DETAILED DESCRIPTION

Figure 1:
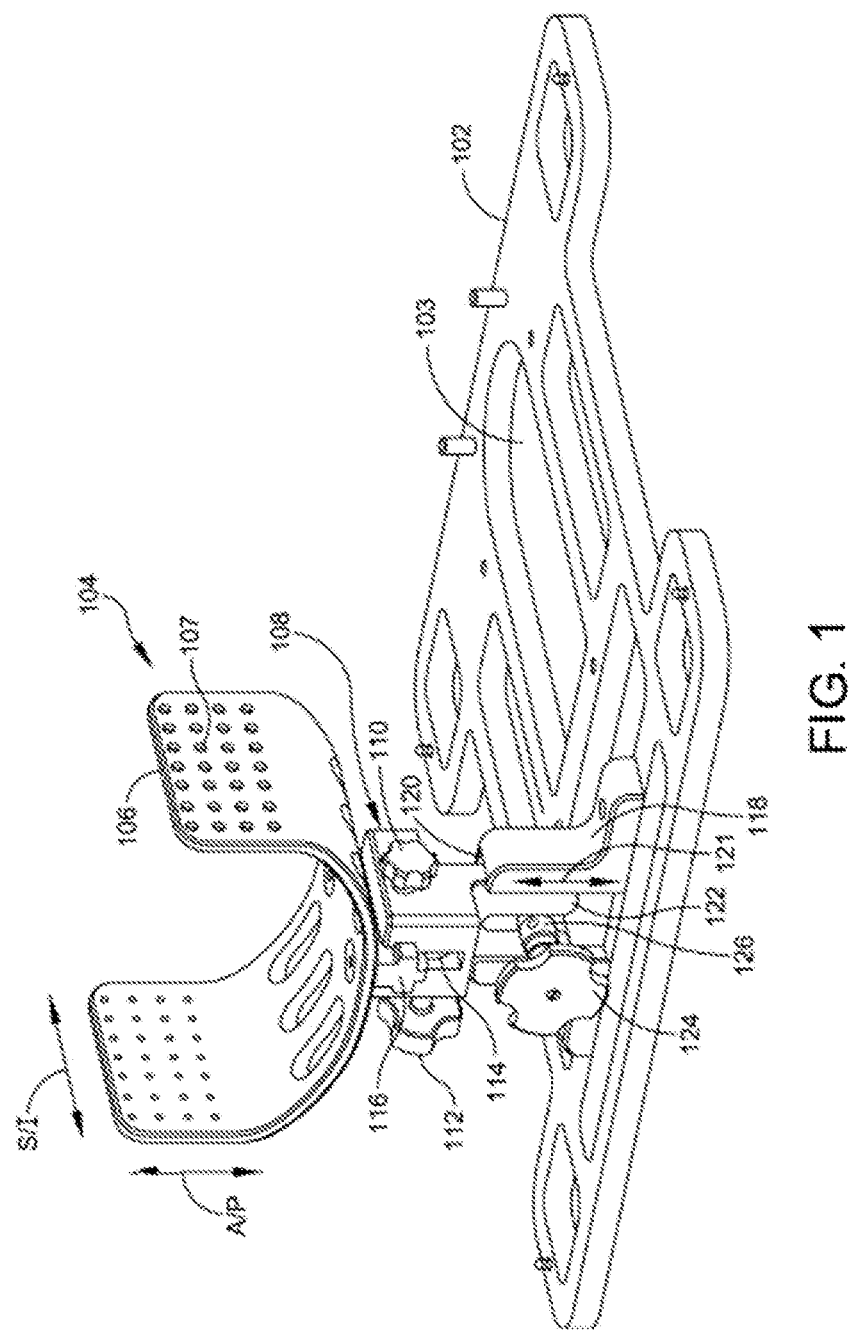
FIG. 1 is an isometric view of a joint space stabilizer assembly on a base plate according to some embodiments of this disclosure.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

This disclosure describes an external fixation apparatus for the foot and tibia, providing ankle joint stabilization, simulated weight bearing, and internal and external foot rotation. The fixation apparatus stabilizes the ankle and restores joint space. The simulated weight bearing feature places the foot bones in position (while in the fixation apparatus) similar to the weight-bearing positions of the bones. The foot rotation function allows rotation of the foot in a transverse plane relative to the tibia after the foot and tibia are fixed by the fixation apparatus. The foot can be rotated after fixation, to establish the mortise view for evaluation. While a patient's foot is fixed in the apparatus, a resection guide cartridge holder is attached to the fixation apparatus. The cartridge holder is configured to align and fix a resection guide or a sizing guide to the foot holder to prepare the tibia and talus for receiving a total ankle prosthesis. If the cut surface of the talus has a void that is to be treated by implantation of a talar plate with an augment, an augment reamer base is pinned to the talus. The reamer base positions and aligns a reamer for enlarging the void to a predetermined size and shape for receiving the augment of the talar plate. The total ankle replacement is implanted while the apparatus fixes the tibia and foot.

Fixation Apparatus

In total ankle revision procedures the ankle joint can become severely destabilized from incompetent ligaments, bone removal, and/or implant removal. A destabilized joint can be extremely difficult for the surgeon to work with, for example, when aligning the bones and placing the implant in vivo. A fixation apparatus described herein gives the surgeon the ability to restore joint space, tension the ligaments, and stabilize the joint.

FIGS. 6, 7, 17 and 18 are isometric views of the fixation apparatus 100. The apparatus 100 comprises a base 102. A foot plate assembly 200 is attached to the base 102. The foot plate assembly 200 has a plurality of members 300 attached to a foot plate 202. The members 300 are configured for receiving at least a first wire or pin 240 to fix a foot of a person relative to the foot plate 202, while the foot plate 202 is oriented normal to a superior-inferior direction of the foot in "simulated weight bearing".

FIGS. 1-16 show components and sub-assemblies of the fixation apparatus 100, which are shown isolated or in partially assembled configurations, for ease of viewing. The various components can be assembled in a variety of sequences. The assembly sequence is not limited to the order shown in FIGS. 1-16.

FIG. 1 is an isometric view of the base 102 with the joint stabilization assembly 104 attached to the base 102. The joint stabilization assembly 104 includes a support (e.g., a tray) 106 shaped to receive a calf of a person, and a positioning assembly 108 for attaching the tray 106 to the base 102. The positioning assembly 108 is coupled to brackets 118 via the lock knob 124 (and the stop 126 attached to the lock knob 124). The brackets 118 are in turn connected to the base 102 using bolts or screws.

In some embodiments, the base 102 is configured to provide a minimal frame for attachment of the joint stabilizer assembly 104, an Achilles support 130, the foot plate assembly 200, and the struts 300. The base 102 has open spaces to avoid any unnecessary restrictions on access to the patient's limb and the components of the fixture by the surgeon.

The support 106 is generally U-shaped, to comfortably support the posterior side of the calf of the patient. The support 106 has a medial wall and a lateral wall. The medial and lateral walls of support 106 are configured for attachment of a wire or pin 244 (FIG. 18) to fix a tibia 250 of the person in the superior-inferior direction relative to the support 106. For example, in some embodiments, the medial and lateral walls of the support 106 have a plurality of openings 107. A wire or pin 244 is passed through openings 107 and through the patient's tibia, while the patient's calf is resting on the support 106, fixing the tibia in the superior-inferior direction and the anterior-posterior direction relative to the support 106.

In some embodiments, the positioning assembly 108 includes a first mechanism 112, 114, 116, such as a gear mechanism, for positioning the support 106 in a superior-inferior direction relative to the base 102. In some embodiments, the support 106 has a rack 116 attached thereto, and the first mechanism includes a pinion 114 for translating the rack 116. In other embodiments (not shown), the first mechanism can include a gearing mechanism, a worm drive, a screw mechanism, a rail slidable within a channel, or the like.

In some embodiments, the positioning assembly 104 further comprises a lock 110 configured to fix a position of the rack 116 in the superior-inferior direction. For example, the lock 110 can include a threaded member (not shown) attached to a knob, such that the end of the threaded member bears against the rack 116 when the knob is turned to advance the threaded member.

In some embodiments, the positioning assembly 108 includes a second mechanism 122, 124, 126 for positioning the support in an anterior-posterior direction perpendicular to the superior-inferior direction. For example, in some embodiments, the second mechanism includes a body 122 attached to the pinion 114. The body 122 has a longitudinal slot. The body 122 is manually slidable within a channel 120 fixed relative to the base 102. A lock knob 124 is turned to advance a stop 126 to apply a bearing force against the body 122 (or turned in the opposite direction to retract the stop 126 and release the body 122). In other embodiments (not shown), a gear mechanism is used to precisely position the body 122 in the anterior-posterior direction.

The channel 120 has a longitudinal axis 121 oriented in an anterior-posterior direction perpendicular to the superior-inferior direction. In some embodiments, the channel 120 is formed by a groove in a respective bracket 118 on each side of the body 122. In other embodiments (not shown), the body 122 has grooves or channels on its medial and lateral edges, and the brackets 118 have rails that are slidably received by the grooves or channels.

Figure 2:
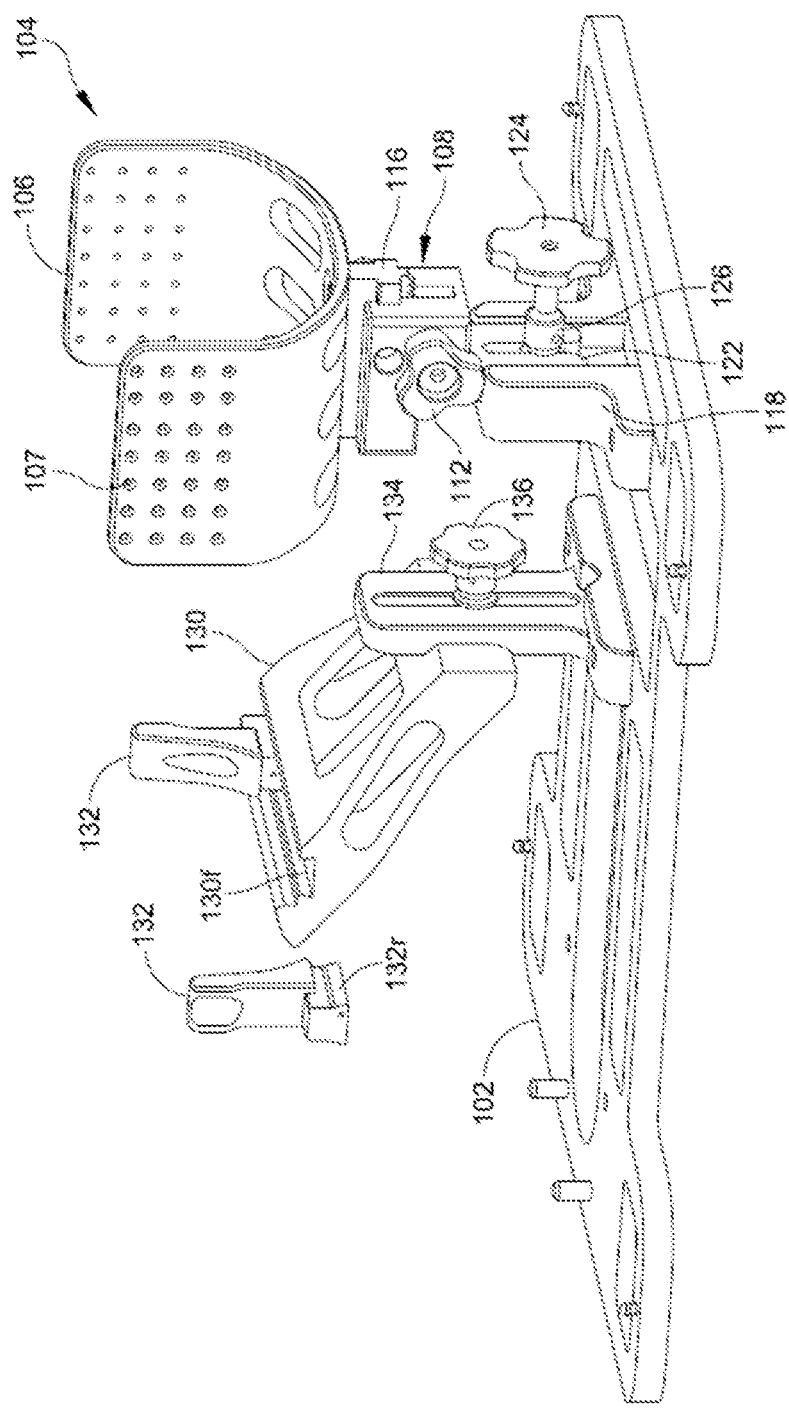
FIG. 2 is an isometric view showing the assembly of FIG. 1, with an exemplary Achilles support attached.

FIG. 2 shows the assembly of FIG. 1, to which the Achilles support 130 is added. In some embodiments, the Achilles support 130 has a pair of adjustable side brackets 132. For example, the Achilles support 130 can have a track 130t which receives a rail 132r on the bottom of each side bracket 132. The rails 132r are slidable within the track 130t for continuously adjusting the distance between the side brackets 132. The combination of the Achilles support 130 and the two side brackets 132 form a U-shaped support for the lower portion of the leg, between the calf and the foot. In some embodiments, the Achilles support 130 is attached to a positioning bracket 134. The bracket 134 has an anterior-posterior slot. An adjustment knob 136 is attached to a threaded member, which passes through the slot and is received by a female thread in the Achilles support 130. The anterior-posterior position of the Achilles support 130 is adjustable by turning the knob 136 to loosen the Achilles support 130, manually adjusting the anterior-posterior position, and tightening the knob 136.

Figure 3:
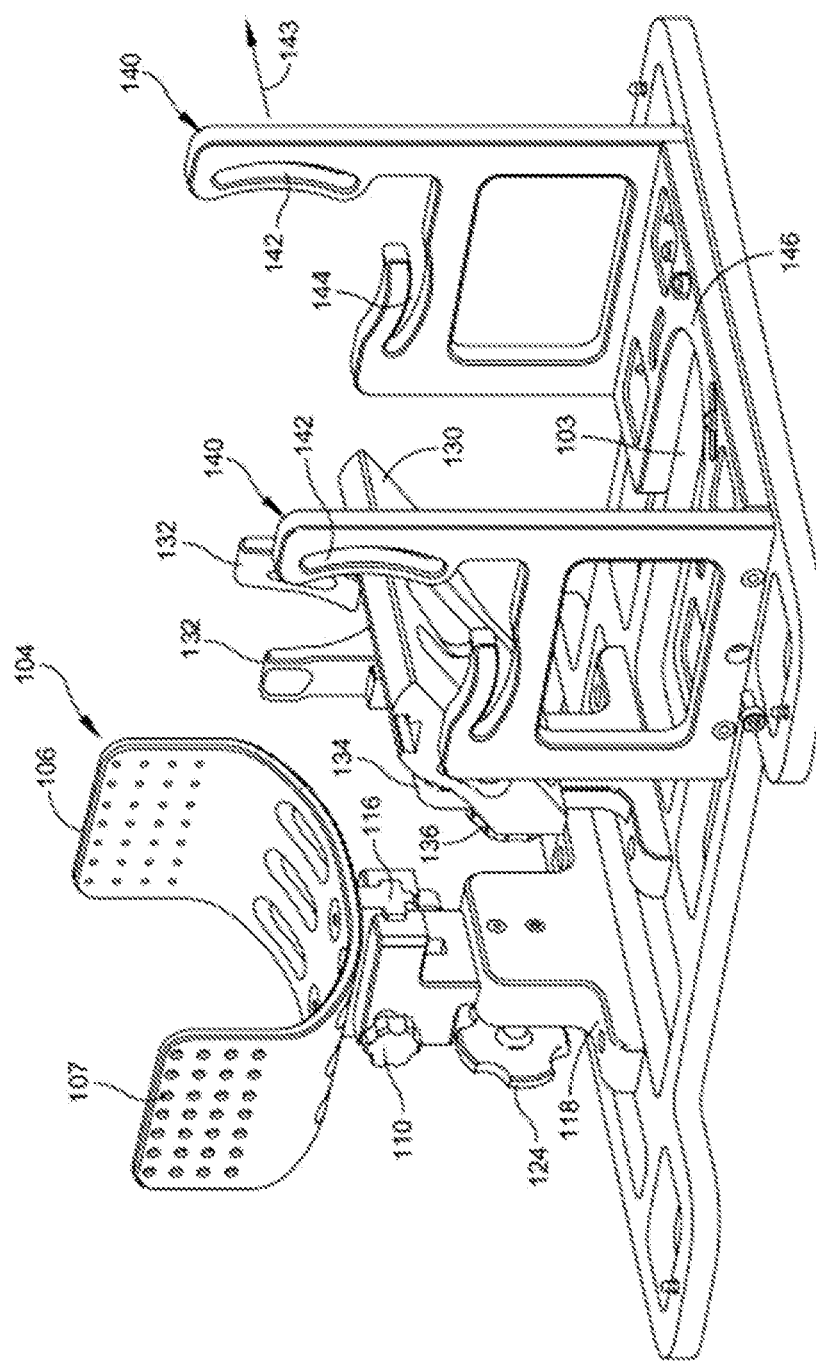
FIG. 3 is an isometric view showing the assembly of FIG. 2, with an exemplary foot holder bracket attached.

FIG. 3 is an isometric view showing a pair of plates 140 assembled to the base 102 of FIG. 2. The plates 140 are attached to medial and lateral sides of a U-shaped bracket 146. The plates 140 are oriented so as to lie in respective parasagittal planes. The U-shaped bracket 146 is attached to the base plate 102 by two U-bracket knobs 147 (FIG. 6) on the posterior side of base 102, to allow manual adjustments without tools. The plates 140 include respective inferior slots 142 and posterior slots 144 for attachment of a base plate assembly 150, discussed below. Both the base plate 102 and the U-shaped bracket 146 have a central opening 103. The central opening 103 permits the surgeon to access the ankle from the posterior side during surgery. In some embodiments, the inferior slots 142 and posterior slots 144 are curved, to permit the base plate assembly 150 to rotate about a medial-lateral axis 143.

Figure 4:
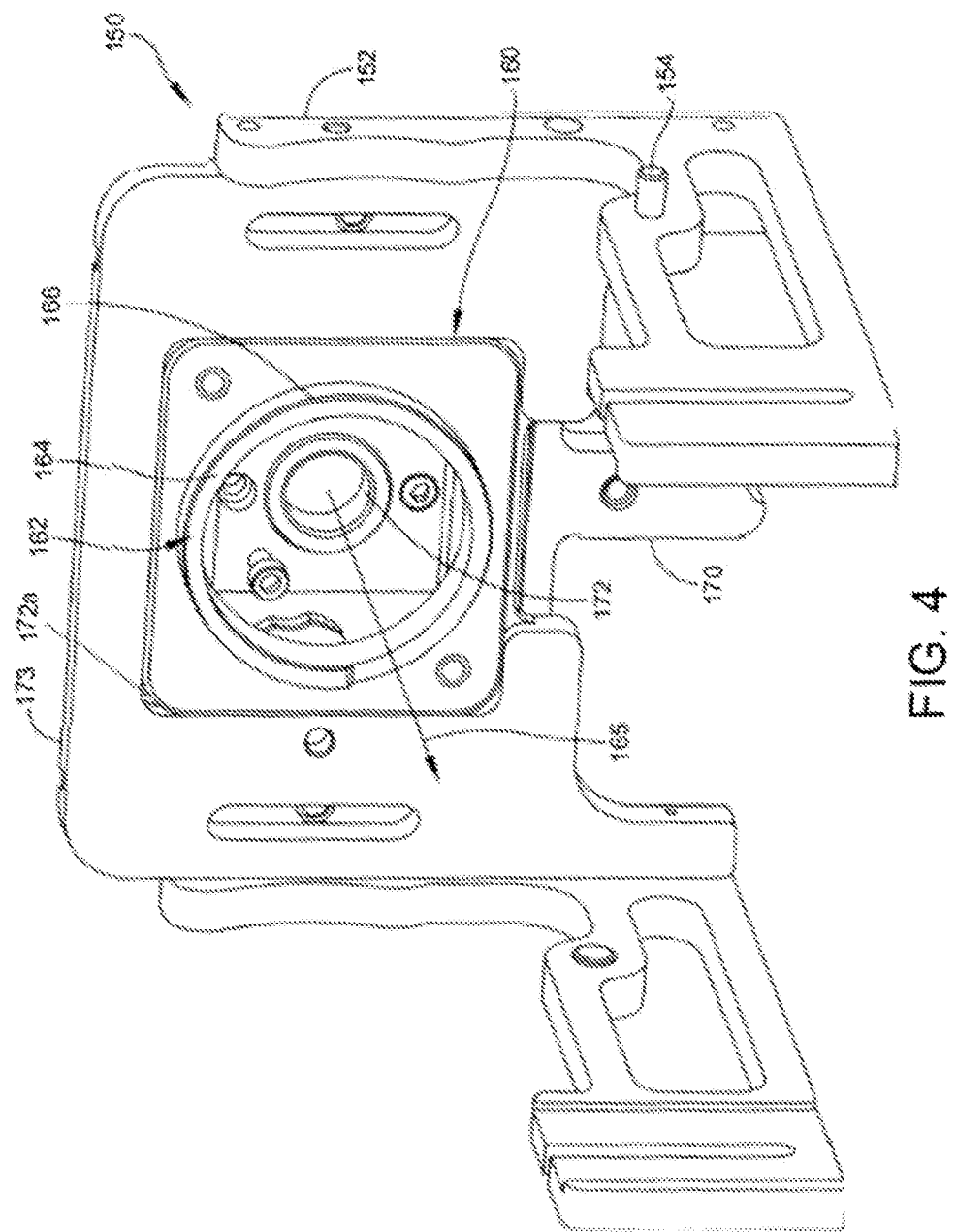
FIG. 4 is a superior isometric view showing a base plate assembly configured to be attached to the foot holder bracket of FIG. 3.
Figure 5:
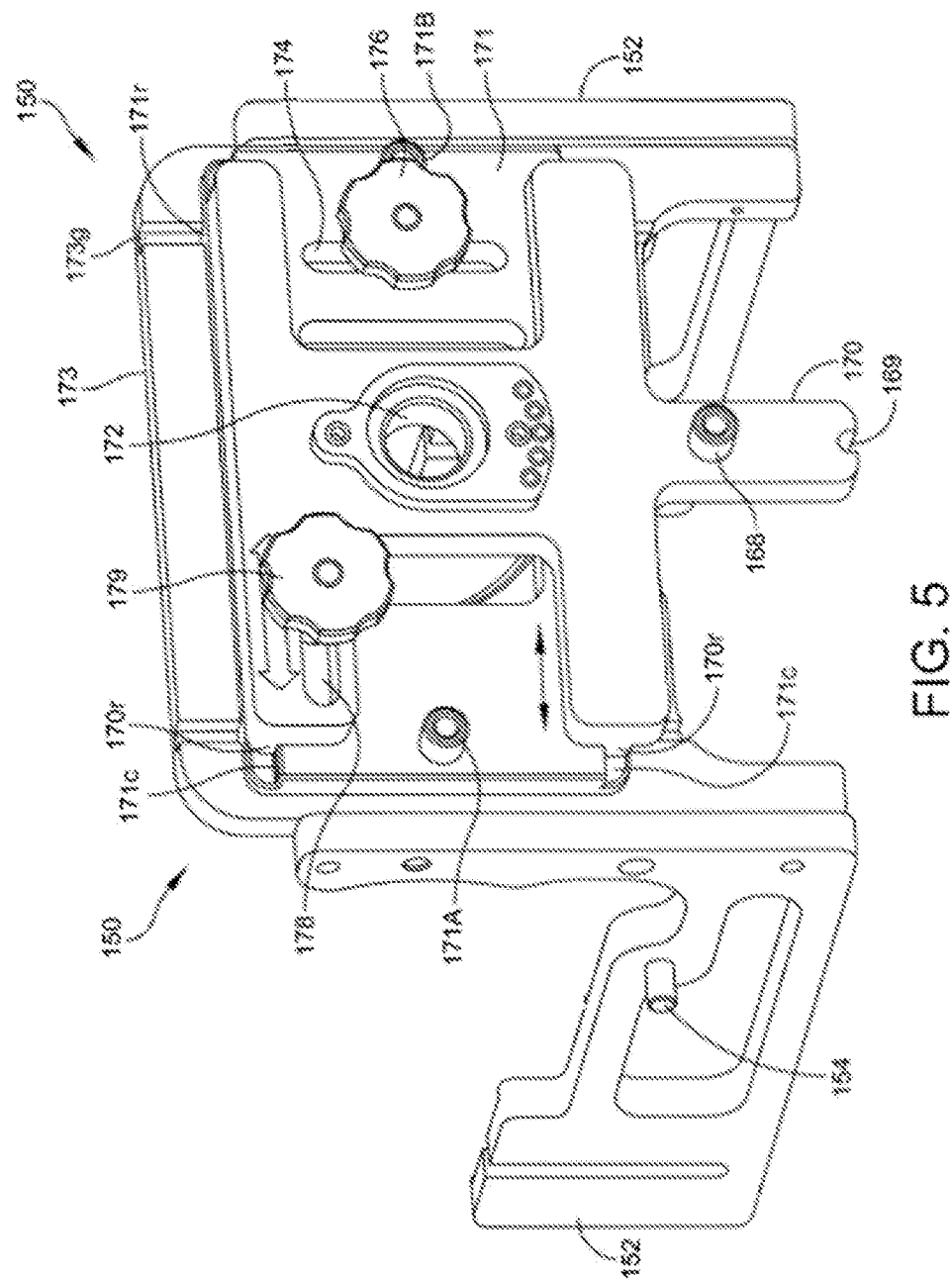
FIG. 5 is an inferior isometric view showing the base plate assembly of FIG. 4.

FIG. 4 is an isometric view of the base plate assembly 150 as seen from the superior side, and FIG. 5 is an isometric view of the base plate assembly 150 as seen from the inferior side. The base plate assembly 150 is configured for holding a foot plate assembly 200 (discussed below), while permitting rotation of the foot plate assembly 200 about the superior-inferior axis 165, translation of the port 172 and 172a in medial-lateral and anterior-posterior directions relative to the foot plate assembly, and rotation of the base plate assembly 150 about the medial-lateral axis 143 (FIG. 3).

The base plate assembly 150 has two side plates 152, which can be generally L-shaped. The side plates 152 are attached to medial and lateral sides of a rotation base plate (inferior plate) 173. The side plates 152 have outwardly-extending pins 154 that are slidably received in the slots 144 of the plates 140. A flexion knob 141 (FIG. 17) comprises a knob attached to a threaded member, which is inserted through the inferior slot 142. Turning the flexion knob 141 advances its threaded member to lock the angular position of the base plate assembly 150 about the medial-lateral axis 143.

As shown in FIG. 5, the base plate assembly 150 has an anterior-posterior adjustment plate 171 attached to the inferior side of the rotation base plate 173. In some embodiments, the rotation base plate 173 has a pair of grooves 173g on the inferior side thereof. The grooves 173g extend in the anterior-posterior direction. The anterior-posterior adjustment plate 171 has corresponding ridges 171r slidably received in the grooves 173g, allowing continuous anterior-posterior adjustment of the port 172. The anterior-posterior adjustment plate 171 has a slot 174 permitting anterior-posterior motion, and a lock knob 176. Advancing the knob 176 locks the anterior-posterior position of plate 171. For example, the knob 176 can have a threaded member (not shown) that is received by the rotation base plate 173, and a washer that bears against the plate 171 when the knob 176 is advanced.

Figure 17:
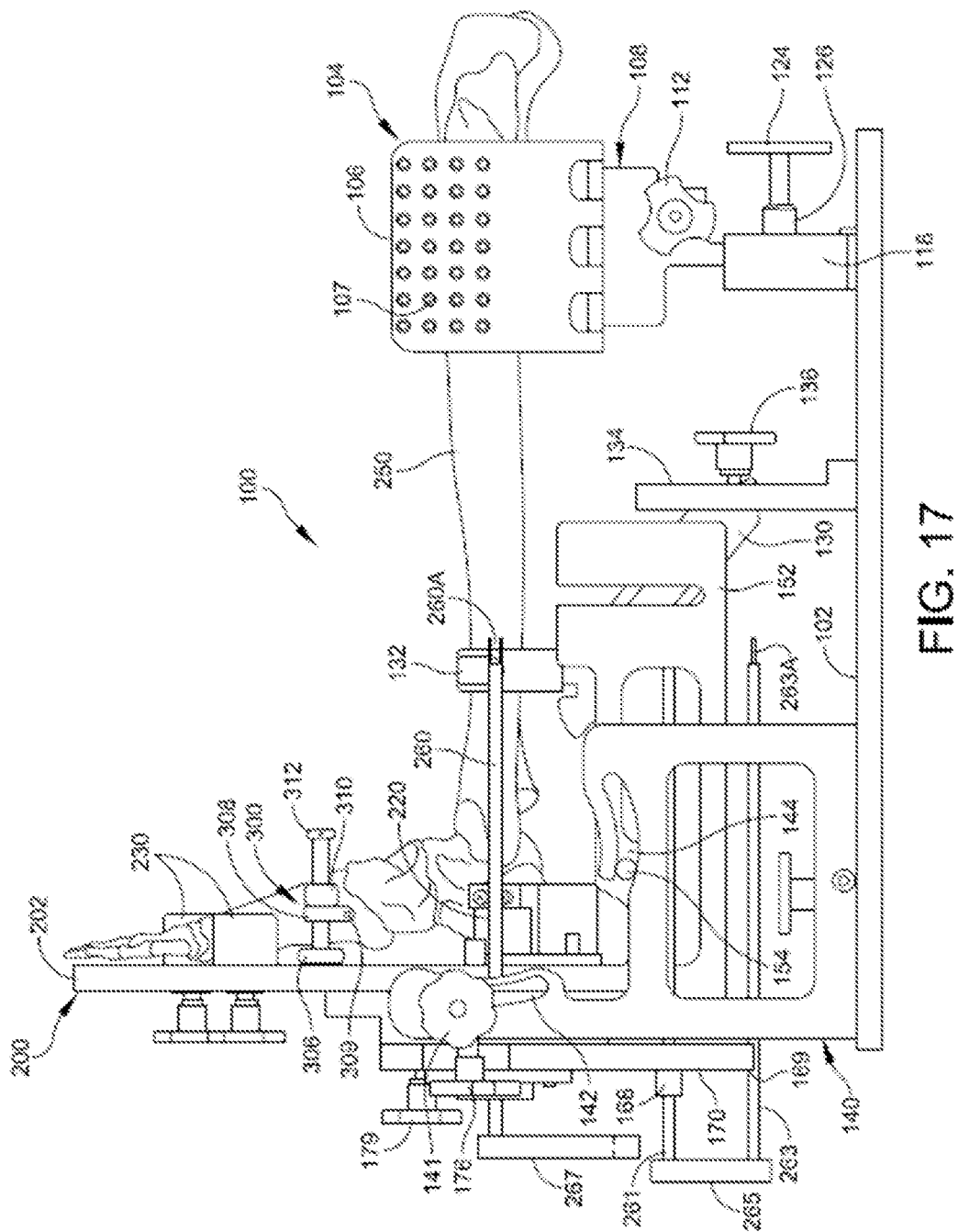
FIG. 17 is a lateral view of the foot holder of FIG. 7, with the foot plate of FIG. 16 attached thereto.
Figure 18:
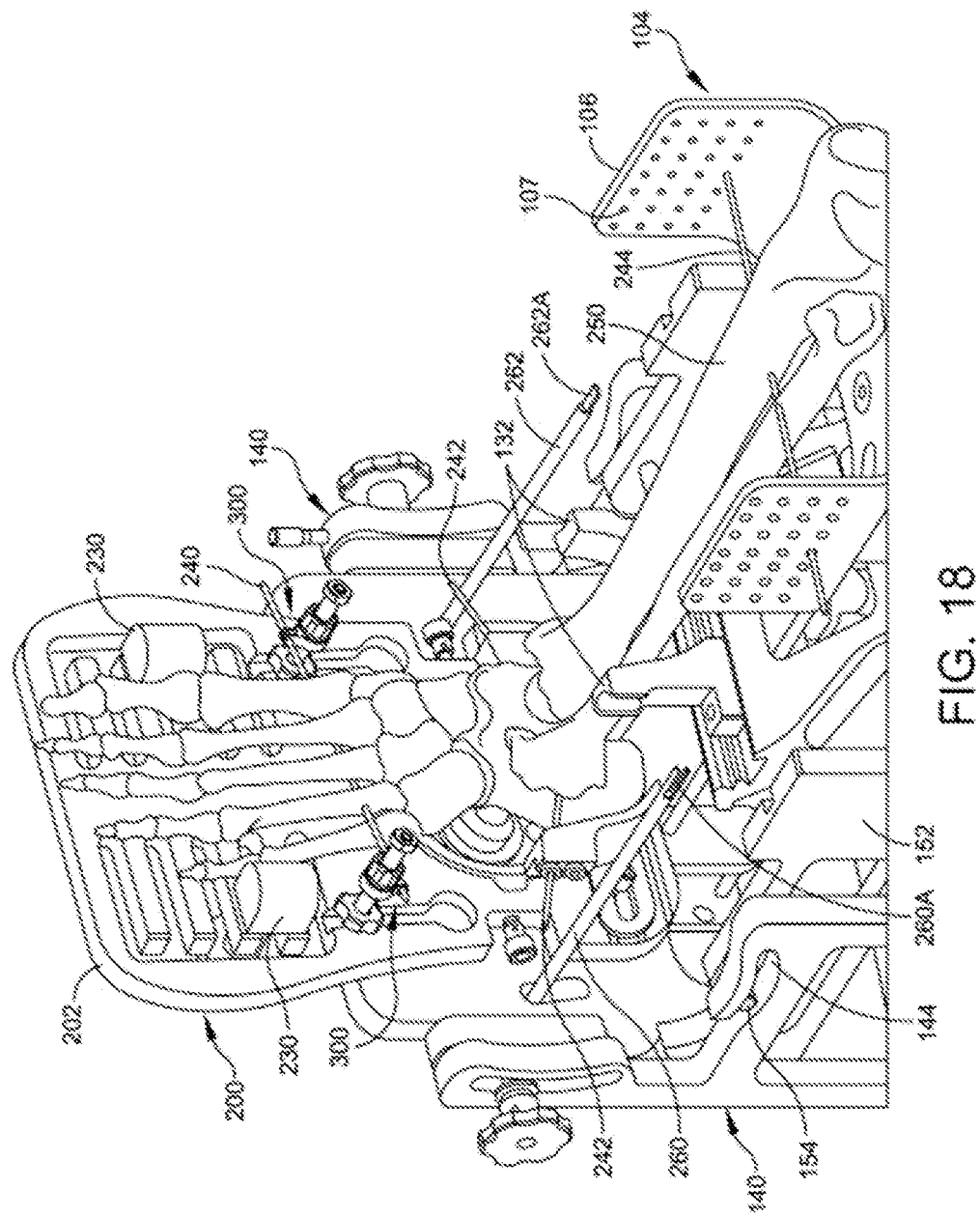
FIG. 18 is an isometric view of the foot plate attached to the foot holder assembly of FIG. 17, showing the medial-lateral alignment members.

The anterior-posterior adjustment plate 171 has a pair of medial-lateral sleeves 171A, 171B. The medial-lateral sleeves 171A, 171B are located along a medial-lateral axis of the anterior-posterior adjustment plate 171. The medial-lateral sleeves 171A, 171B are adapted to receive a pair of medial-lateral alignment members or rods 260, 262 (FIGS. 17, 18).

A medial-lateral adjustment plate 170 is adjustably attached to the inferior side of the anterior-posterior adjustment plate 171. In some embodiments, the anterior-posterior adjustment plate 171 has two channels or grooves 171c (e.g., on the anterior and posterior sides thereof); the medial-lateral adjustment plate 170 has two ridges or rails 170r that are received by the respective channels or grooves 171c.

This allows the medial-lateral adjustment plate 170 to slide in the medial-lateral direction relative to the plate 171. The medial-lateral adjustment plate 170 has a slot 178 permitting medial-lateral motion, and a lock knob 179. Advancing the knob 179 locks the medial-lateral position of plate 170. For example, the knob 179 can have a threaded member (not shown) that is received by the anterior-posterior adjustment plate 171, and a washer that bears against the plate 170 when the knob 179 is advanced.

In some embodiments, the anterior-posterior adjustment plate 171 and the medial- lateral adjustment plate 170 have a port 172 extending therethrough, permitting the surgeon to insert a cannula and trocar (or other surgical tool) into the calcaneus from the inferior side of the apparatus 100. The anterior-posterior adjustment plate 171 and medial-lateral adjustment plate 170 allow the surgeon to position the port 172 relative to the axis of the foot plate assembly 200.

In some embodiments, the medial-lateral adjustment plate 170 has a sleeve or socket 168 and an opening or cutout 169 aligned with each other along the anterior-posterior axis of the medial-lateral adjustment plate 170. The sleeve 168 and opening or cutout 169 are adapted to receive a pair of anterior-posterior alignment members or rods 161, 163 (FIG. 17). In other embodiments (not shown), two sleeves 168 can be substituted for the single sleeve 168 and the opening or cutout 169.

Figure 6:
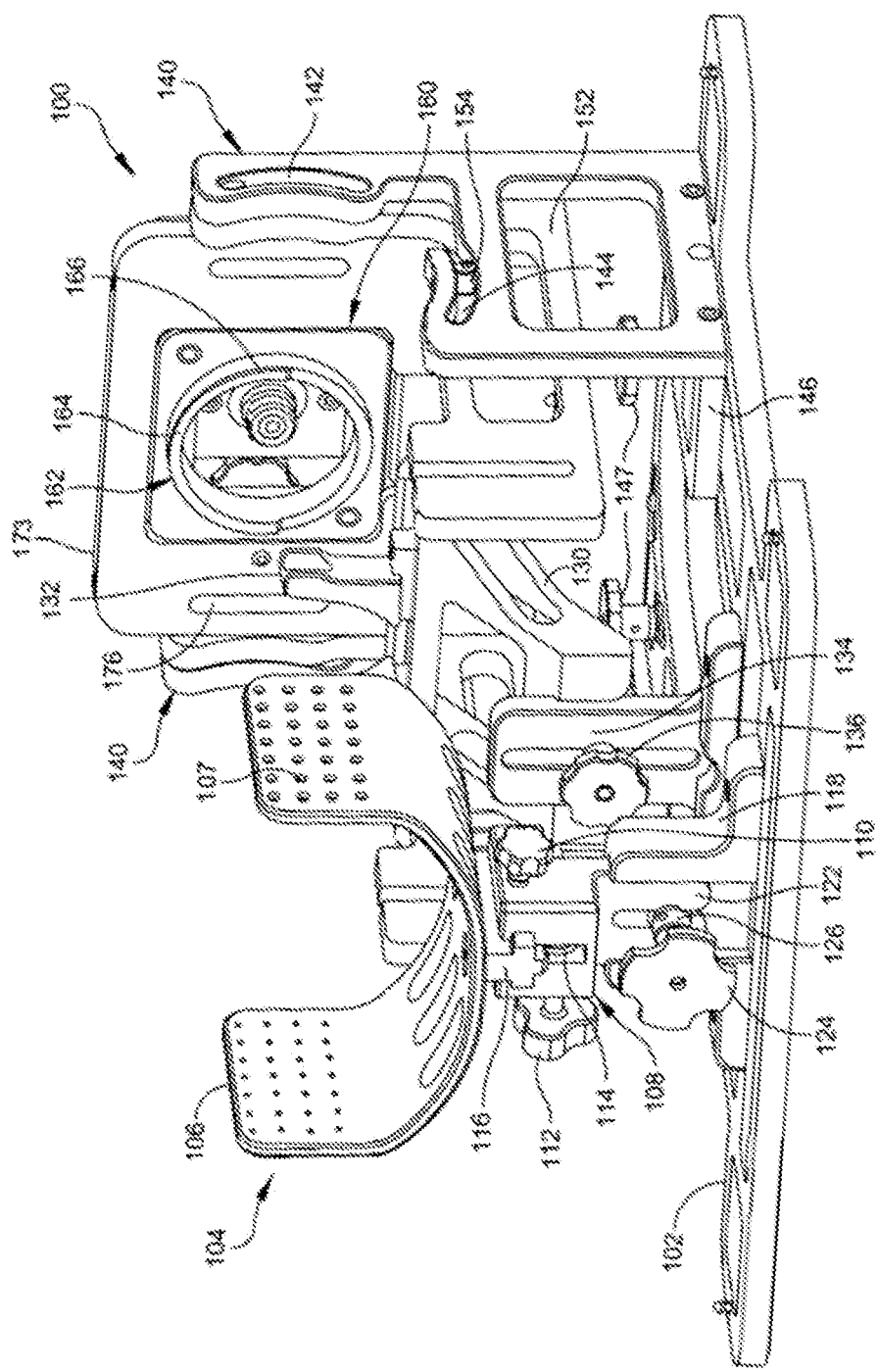
FIG. 6 is a superior isometric view showing the assembly of FIG. 3, with the base plate assembly of FIGS. 5 and 6 attached thereto.
Figure 7:
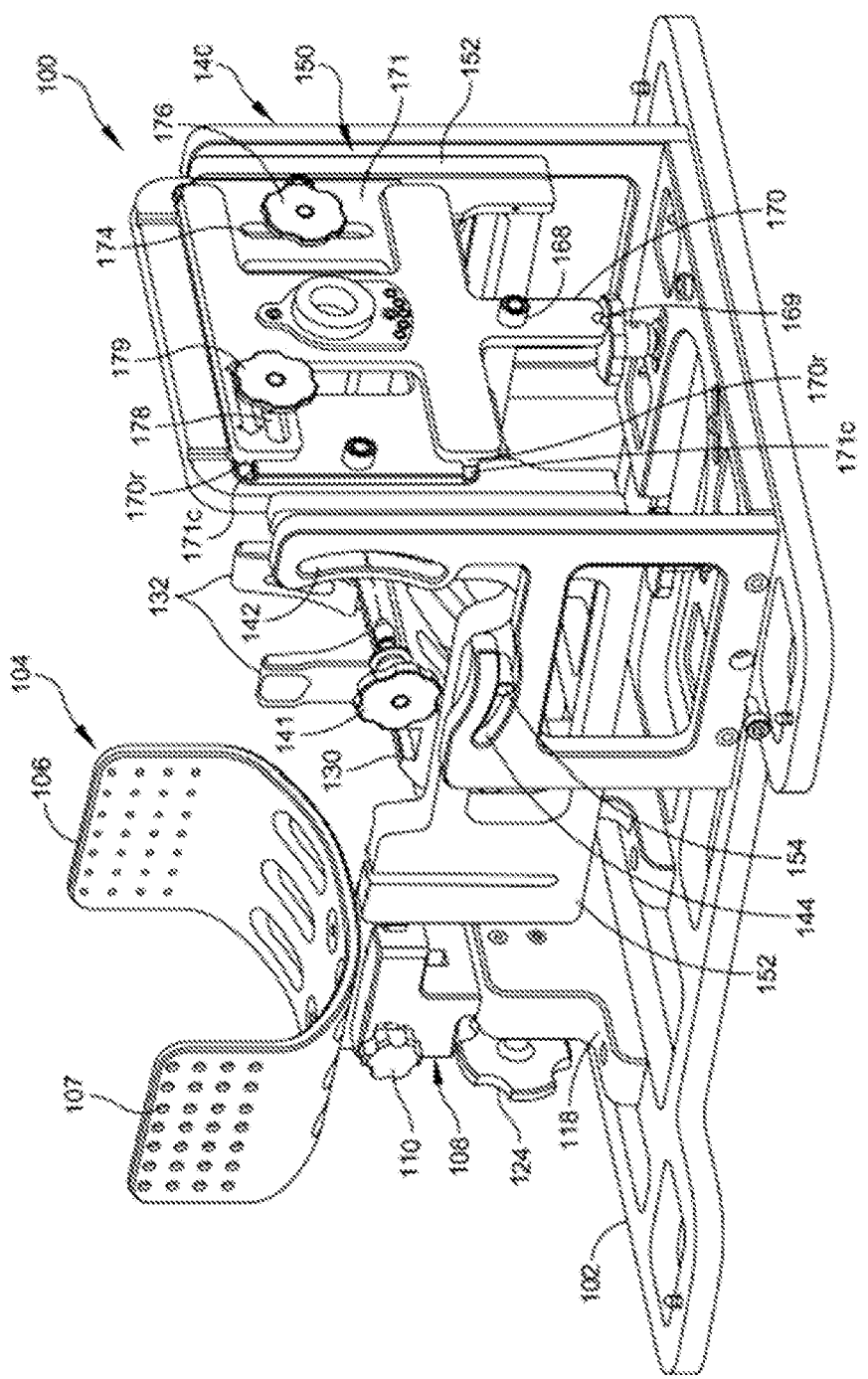
FIG. 7 is an inferior isometric view of the assembly of FIG. 6.

As shown in FIGS. 4 and 6, the rotation base plate 173 has a retaining body 162, such as a mounting ring 164, for rotatably mounting the foot plate assembly 200 (FIGS. 8-16). The ring 164 has an outside surface with a groove 166 therein.

FIGS. 8-16 show the foot rotation plate assembly 200. The base 102 has a rotation plate 173 with a circular retaining body 162, such as ring 164, and the foot plate 202 has a circular opening 209 adapted to receive the retaining body 162. In some embodiments, the retaining body 162 includes a ring 164 with a groove 166 on a side edge thereof, and the foot plate 202 has at least one locking pin 210 that is positionable within the groove 166 to prevent translation of the foot plate 202 relative to the retaining body 162, but permit rotation of the foot plate relative to the retaining body. In some embodiments, a position of the rotation plate 173 is adjustable in the anterior-posterior direction relative to the base 102.

Figure 8:
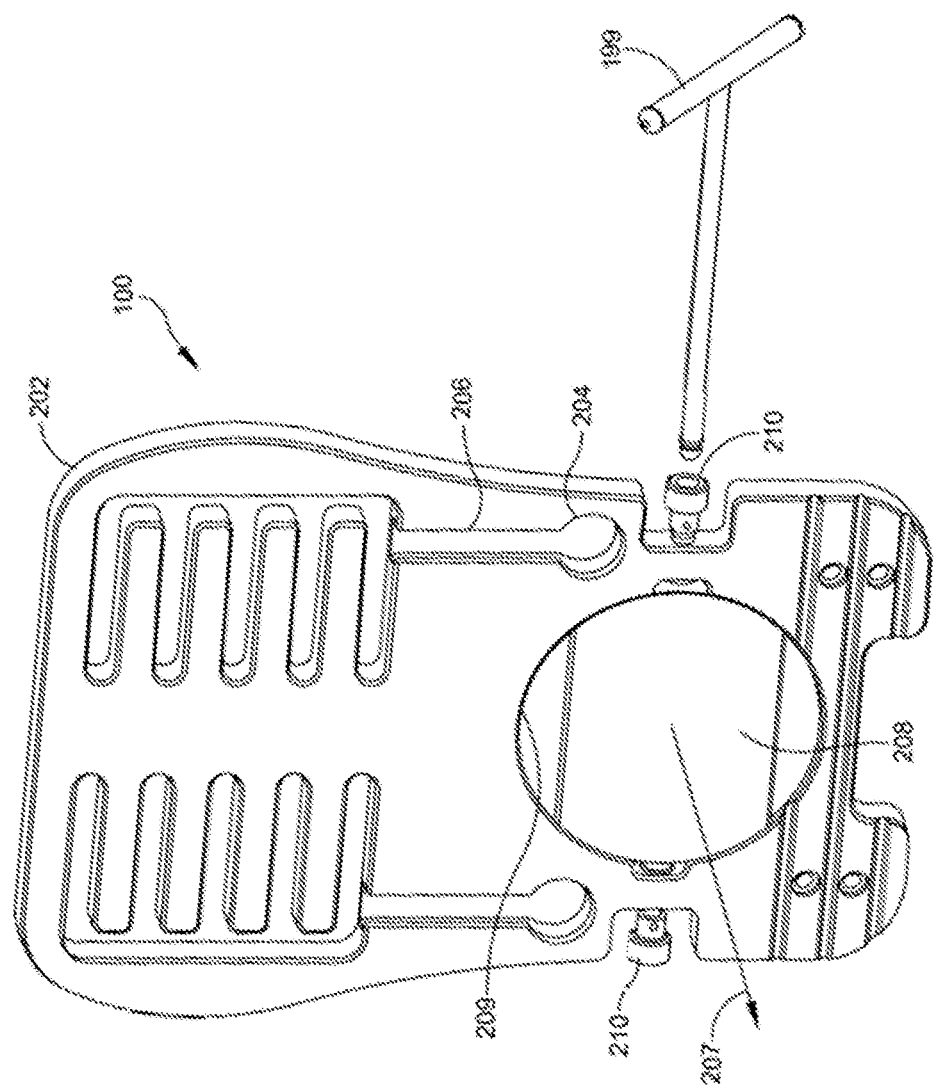
FIG. 8 is a superior view of a foot plate before removal of the heel support and attachment to the base plate assembly of FIG. 7.

As shown in FIGS. 8-10, the assembly 200 has a plate 202. The plate 202 has a circular opening 209 configured to be mounted around the ring 164 of the rotation base plate 173. A pair of screws 210 having bosses 212 on the ends thereof are threadably received in the medial and lateral side edges of the foot plate 202. The bosses 212 are adapted to engage the groove 166 on the outside surface of the mounting ring 164 when the screws 210 are advanced (e.g., by turning the screws 210 with a suitable wrench 199). Loose engagement between the bosses 212 and the groove 166 holds the foot plate assembly 200 on the mounting ring 164, while permitting the foot plate assembly 200 to rotate around an axis 207 (FIG. 8). Tightening the screws 210 locks the rotation angle of the foot plate assembly 200 relative to the base 102. The foot plate 202 is configured to have its axis of rotation 207 aligned with the tibia 250 while the foot plate is attached to the base 102 and the tibia 250 is secured to the support 106. This is a non-limiting example. In other embodiments, a different mechanism is used to pivotally mount the foot plate 202 to the rotation base plate 173. For example, in some embodiments (not shown), the foot plate has a ring, and the rotation base plate has an opening that receives the ring. In other embodiments, the rotation base plate has a ball head permitting the foot plate to pivot and/or rotate.

In some embodiments, as shown in FIGS. 8-12, 15 and 16, a detachable heel support 208 is inserted in the foot plate 202 while the foot is being fixed to the foot plate. The heel support 208 has an outer edge 208e with a groove matching the groove 166 on the outer edge of the mounting ring 164.

FIG. 10 is a cross-sectional view of the foot plate 202, while the detachable heel support 208 is in place. In FIG. 10, one boss 212 engages the outside edge 208e of the heel support 208, while the other screw 210 is still retracted. A cross-sectional view of the foot plate 202 while the foot plate is attached to the mounting ring 164 of the fixation apparatus 100 would look similar to FIG. 10, except that in FIG. 10, the heel support 208 is a solid disk, but the mounting ring 164 is a hollow cylindrical shell when viewed in cross-section.

Simulated Weight Bearing

When surgeons assess alignment and orientation of bone in the clinical setting they may wish to view weight bearing x-rays. The bones of the foot shift position depending on whether the ankle is weight bearing or non-weight bearing. The degree of joint degeneration and evaluation of the ankle mortise can be underestimated when x-ray is performed on non-weight bearing ankles. Furthermore an accurate measurement of the extent of cartilage involvement and a more dynamic picture of the status of the ankle and hindfoot is achieved in weight bearing x-rays. Thus, the ability to simulate the bone positions of a weight bearing foot provides valuable information to the surgeon.

Figure 11:
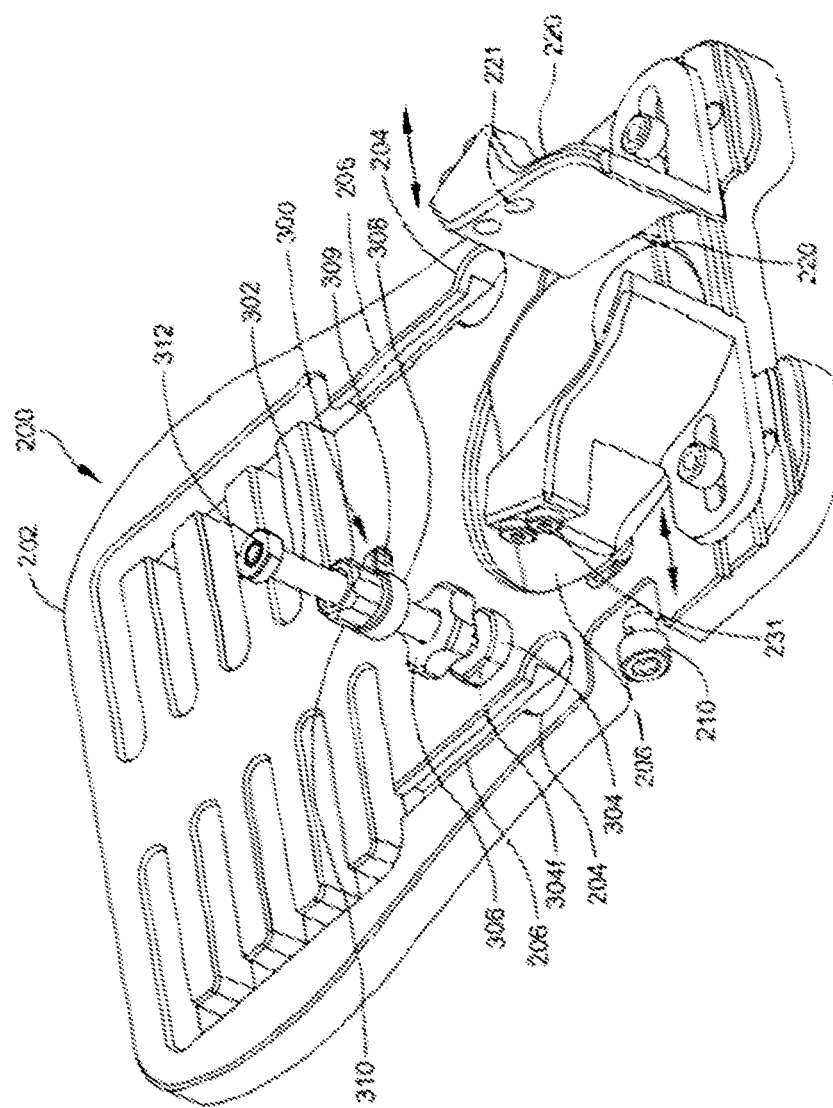
FIG. 11 is an isometric view of the foot plate of FIG. 8, with heel brackets attached thereto.
Figure 12:
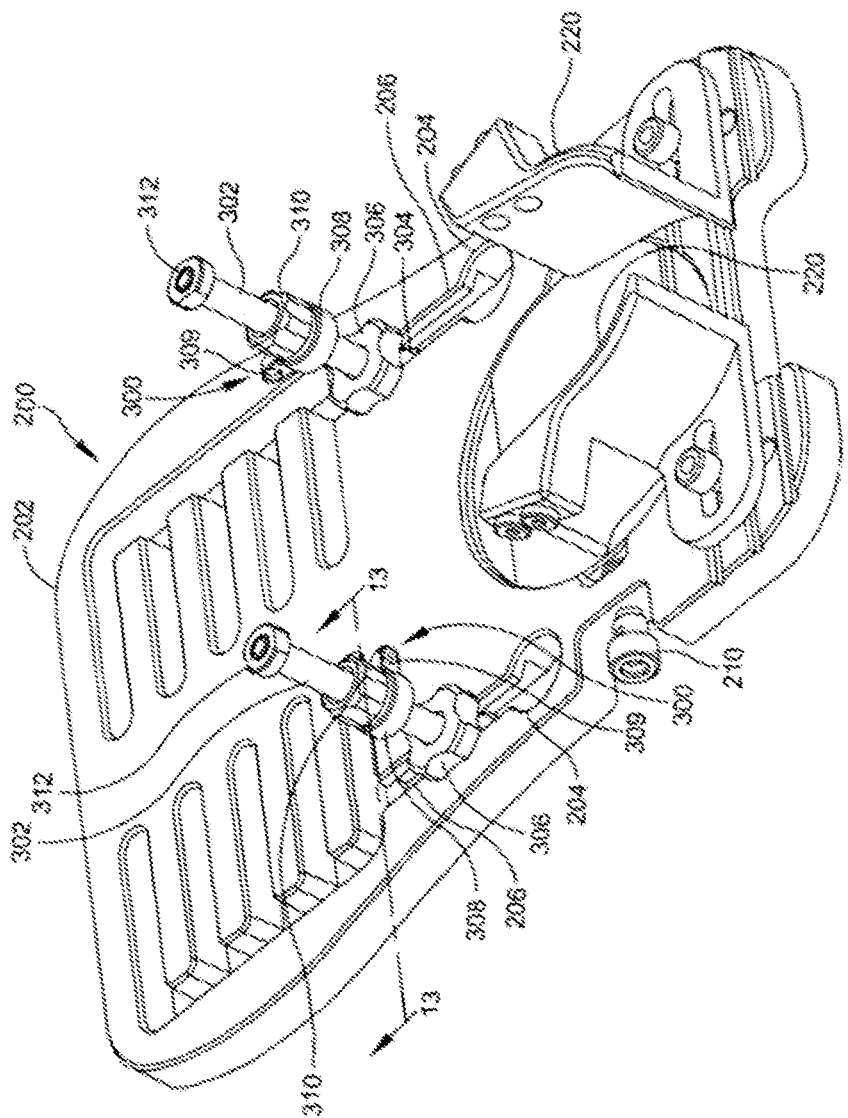
FIG. 12 is an isometric view of the foot plate of FIG. 11, with compression members attached thereto.

Some embodiments comprise a plurality of independently positionable members 300 for retaining wires or pins 240, and for urging the first wire or pin 240 in an inferior and/or anterior direction relative to the foot plate 202. In some embodiments, the members 300 are struts as shown in FIG. 13A. The plate 202 includes two strut mounting channels 204, 206. The channels 204, 206 are configured to receive the members (struts) 300 shown in FIGS. 11-14. FIG. 11 shows one of the struts 300 prior to inserting the strut in the foot plate 202. FIG. 12 shows two of the struts 300 after insertion into the channels 206 of foot plate 200. FIG. 13A is a cross-sectional view of the strut 300 mounted in one of the channels 206.

The plurality of struts 300 each include a threaded member 302. The threaded member 302 has a head 304 configured to slide along a respective anterior-posterior track 206t in the foot plate. The width of the track 206t is smaller than the diameter of the entrance 204. In some embodiments, the head 304 has two flat sides 304f sized to fit the track 206t. Once the head 304 is moved from the channel entrance 204 to the track 206t, the head 304 and the threaded member 302 are prevented from rotating. FIG. 14 shows the proper rotational position of the strut 300 for insertion into the channel entrance 204, with the flat sides 304f of the head 304 of the strut 300 parallel to the anterior-posterior track 206t of the plate 202.

The strut 300 has a lock 306 for fixing the location of the strut along the track 206t thereof. For example, the lock 306 can be a threaded nut that is advanced against the top surface of the plate to grip the plate. FIG. 12 shows the plate 202 after the two struts 300 are inserted in the tracks 206 and the locks 306 are tightened to fix each of the struts in the anterior- posterior direction.

The strut 300 has a guide 308 for receiving the wire or pin 240. In some embodiments, the guide 308 is not threaded, and is slidable along the threaded member 302 of the strut 300 for controlling a position of the wire or pin 240 in the superior-inferior direction. In some embodiments, the guide 308 has an eyelet 309 for receiving the wire or pin 240. When the guide 308 is aligned in the anterior posterior direction, a wire 240 extending in the medial lateral direction can be passed through the eyelet 309 (as shown in FIG. 18). Movement of the guide 308 in the inferior direction causes compression of the bones of the mid-foot against the foot plate 202, simulating a weight-bearing condition.

A compression knob 310 is provided for advancing the guide 308 in the inferior direction. For example, the compression knob 310 can be a threaded nut for urging the guide 308 (and the wire or pin 240 passing through the eyelet of the guide 308) in the inferior direction toward the foot plate 202. In some embodiments, the strut 300 further comprises a retaining nut 312, to prevent any of the components 306, 308 or 310 from separating from the threaded member 302.

FIGS. 14A-14C show an alternative design of a compression member 1400 according to some embodiments. The compression member (or strut) 1400 can be substituted for the strut 300 without any change to the footplate 202. The compression member 1400 has a treaded member 1402 with a head 1422. The head 1422 can have the same shape and function as the head 304 described above. A compression nut 1420 is provided for gripping the foot plate 202 between the compression nut 1420 and the head 1422, as described above with respect to the lock 306 of strut 300. An alignment member 1410 holds a pin or wire (not shown), which passes through the alignment opening 1412. A compression knob 1404 is turned to advance the alignment member in the inferior direction, to compress the foot in the simulated weight bearing position. The compression knob 1404 has a relatively large head 1406 to be gripped by hand, an inferior ring 1408, and a neck 1409 between the head 1406 and ring 1408 for receiving the alignment member 1410. The alignment member 1410 is placed around the neck 1409, and a dowel pin 1414 is inserted through the alignment member 1410. The neck 1409 of the compression nut 1420 is held between the alignment member 1410 and the dowel pin 1414, allowing the alignment member to be advanced in the inferior direction or moved in the superior direction without rotating the alignment member 1410 around the compression member 1400. The strut 1400 also allows compressing or tensioning the bones of the mid-foot.

In some embodiments, the foot plate 202 has a pair of heel brackets 220 that are continuously adjustable in the medial-lateral direction for supporting the medial and lateral sides of the heel. For example, the heel brackets 220 can each have a medial-lateral slot. A respective screw is inserted through the slot, and attaches each heel brackets 220 to the plate 202. In some embodiments, the heel brackets 220 include apertures 221 to permit insertion of wires or pins 242 through the brackets 220 and into the calcaneus. Sleeves 231 can be inserted into the apertures 221 to guide the wires or pins 242. The surgeon can select an appropriately sized sleeve 231 to accommodate a wire or pin of the size the surgeon intends to use.

Figure 15:
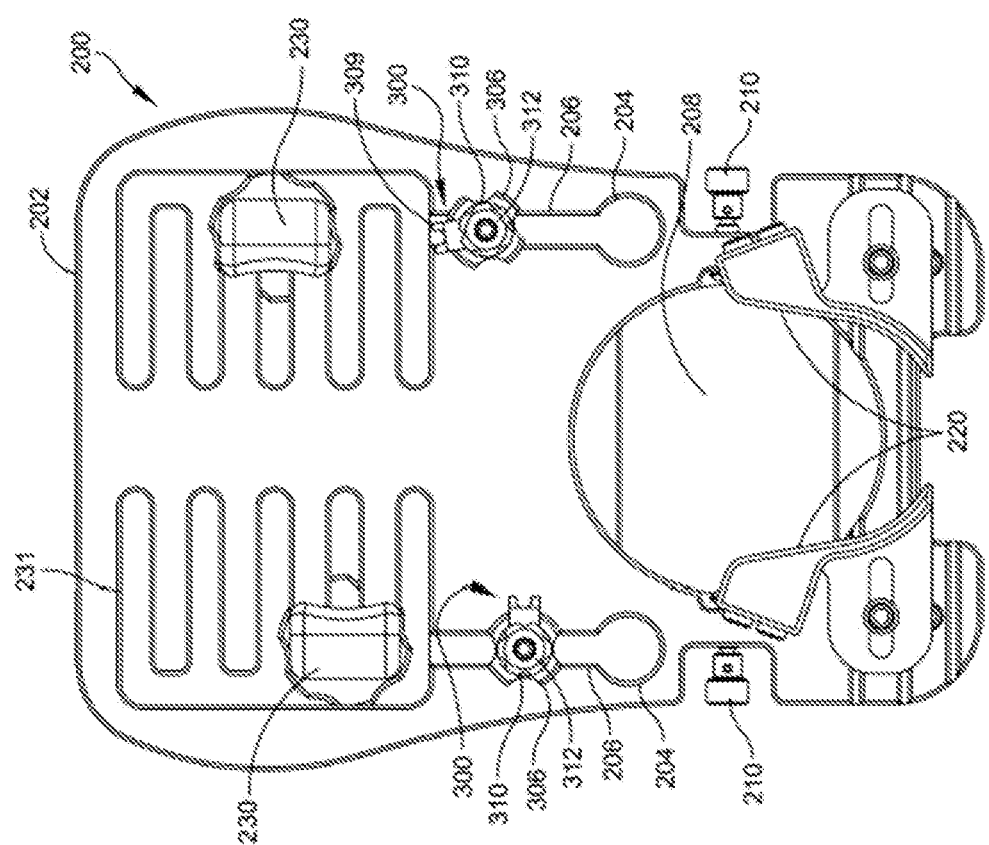
FIG. 15 is a superior view of the foot plate of FIG. 12, with mid-foot supports and compression members attached thereto.
Figure 16:
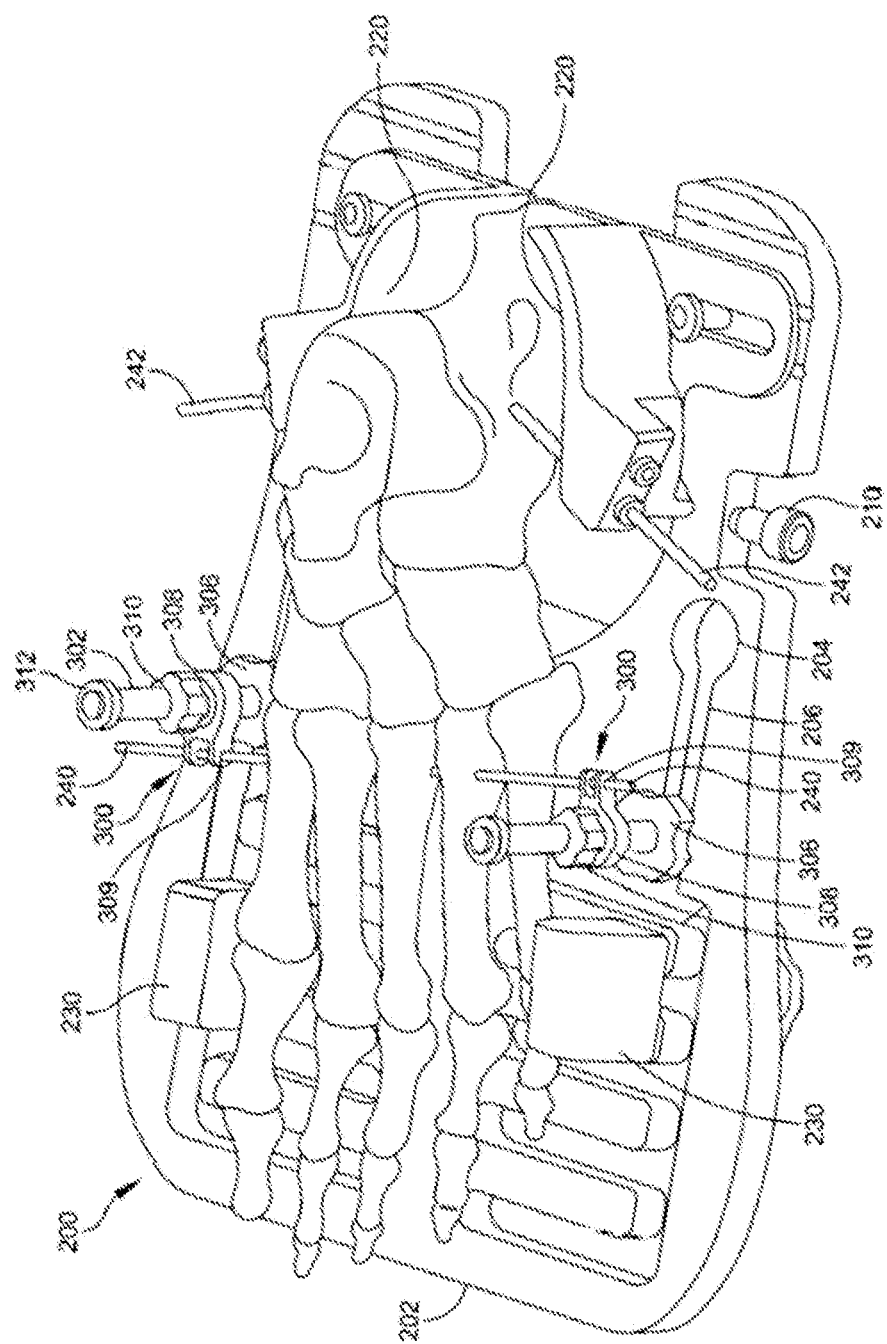
FIG. 16 is an isometric view of the foot plate of FIG. 15, with a foot pinned thereto.

In some embodiments, as shown in FIGS. 15 and 16, a pair of forefoot brackets 230 are mounted to slots 231 in the foot plate 202 for providing additional support to the medial and lateral sides of the foot. In various embodiments, the slots 231 can include one or more medial-lateral slots and/or one or more anterior-posterior slots. The brackets 230 can be positioned along any of the slots 231 by tightening a knob (not shown) on the inferior side of the foot plate 202, to grip the foot plate 202.

FIG. 16 shows the foot fixated by the foot plate 202, prior to attachment of the foot plate assembly 200 to the foot holder 100. The patient's foot is placed at the center of the foot plate assembly 200 so the heel is directly over the heel support 208. The heel brackets 220 are adjusted to enclose and support the heel. The forefoot brackets 230 are adjusted to secure the forefoot. The calcaneus is pinned by the wires or pins 242, which pass through the collars of the heel brackets 220. The struts 300 are positioned along their respective channels 206 (without tightening the locks 306), so that a wire or pin 240 can be placed transversely across the midfoot bones. The wire or pin 240 is driven through the eyelets 309 of the guides 308 and the midfoot bones as shown. The struts 300 are then locked in position against the foot plate 200 by rotating the locks 306 to advance the locks 306 against the top surface of the plate 202. The wire or pin 240 is cut (e.g., with a pin cutter) or bent, and the compression knobs 310 are rotated to drive the guides 308 in the inferior direction toward the plate 202 and compress the midfoot to the foot plate 202, thereby positioning the bones to simulate their weight bearing state.

The screws 210 are retracted to release the heel support 208, and the heel support is removed. The foot plate 202 is now ready for attachment to the foot holder 100. To attach the foot plate assembly 200 to the rotation base plate 173 of the foot holder 100, the ring 164 of the rotation base plate 173 is aligned to the hole 209 in the foot plate 202 (from which the heel support 208 has now been removed). Using the appropriate tool (e.g., hex key 199 of FIG. 8), the screws 210 are advanced sufficiently to loosely engage the groove 166 on the outside of the ring 164, so that the foot plate assembly 200 is held by the ring 164 of the foot plate holder 100, but can be rotated around an axis 165 at the center of the ring 164.

FIGS. 17 and 18 show the complete fixation apparatus 100, with the patient's tibia and foot bones included for reference. Skin and soft tissue are omitted from the drawings, but the position of the bones shown in the figures are the positions the bones would occupy if the skin and soft tissues are present.

As shown in FIGS. 17 and 18, the foot plate 202 is attached to the base 102. The foot plate 202 has a plurality of members 300 attached thereto. The members 300 are configured for receiving at least a first wire or pin 240 to fix a foot of a person relative to the foot plate 202, while the foot plate 202 is oriented normal to a superior-inferior direction of the foot. The foot plate 202 is rotatable relative to the base 102 while the foot plate 202 is attached to the base 102.

A joint stabilizing assembly 104 is attached to the base 102. The assembly 104 includes a support 106 shaped to receive a calf of a person, and a positioning assembly 108 for attaching the support 106 to the base 102. The support 106 is adapted to receive a wire or pin 244 for securing the tibia 250 of the patient. The positioning assembly 108 includes a first mechanism 112, 114, 116 for positioning the support 106 in a superior-inferior direction relative to the base 102.

The foot positioning apparatus of FIGS. 17 and 18 is suitable for fixation during a procedure for implanting a full ankle implant 700 (FIG. 38) comprising a talar component 704-705 configured to be attached to a talus 272 of the person while the foot is fixed relative to the foot plate 202, and a tibial component 701-703 configured to be attached to a tibia 250 of the person while the calf is received by the support 106, where the tibial component 701-703 is configured for articulating motion relative to the talar component 704-705. In other embodiments, the implant or portion thereof can be inserted outside of the apparatus after its position is determined.

In some embodiments, as shown in FIG. 17, a pair of anterior-posterior alignment members 261, 263 are received by the sleeve 168 and the cutout or opening 169 of the medial-lateral adjustment plate 170. The anterior-posterior alignment members 261, 263 extend in the superior direction from the medial-lateral adjustment plate 170. In FIG. 17, only the finger 263A at the superior end of the anterior-posterior alignment member 263 is visible, and the alignment fingers 261A of anterior-posterior alignment member 261 is hidden behind side plate 152. In some embodiments, the anterior-posterior alignment members 261, 263 are both attached to a bar 265 for ease of handling.

Figure 19:
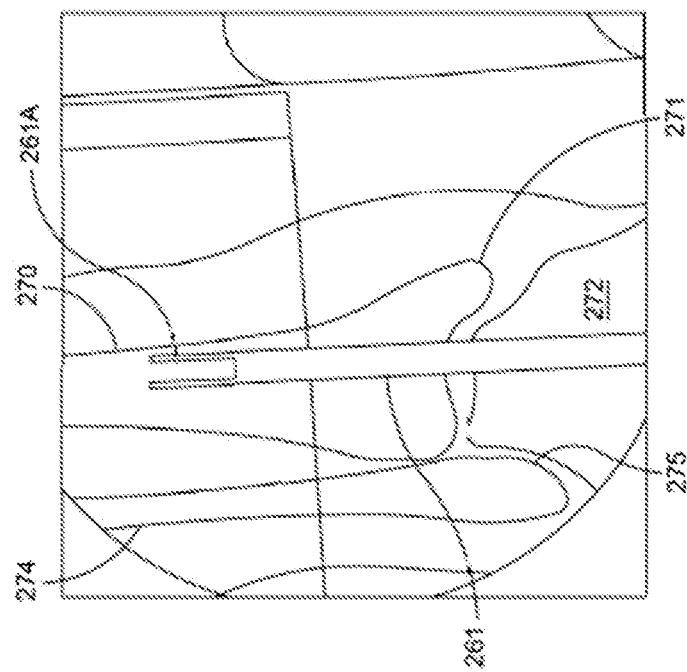
FIG. 19 is an anterior fluoroscopic image of the ankle with the anterior-posterior alignment members properly aligned for mortise view.
Figure 20:
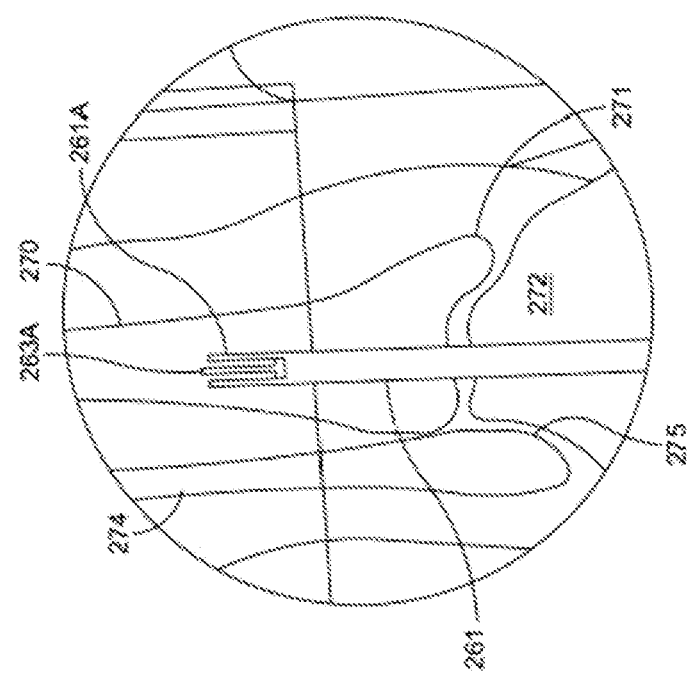
FIG. 20 is an anterior fluoroscopic image of the ankle with the anterior-posterior alignment members improperly aligned with each other and with the tibia.

The anterior-posterior alignment members 261, 263 have alignment features 261A, 263A, respectively. In some embodiments, the alignment features 261A include two fingers extending in the superior direction on medial and lateral sides of the tip of anterior-posterior alignment member 261. The alignment feature 263A include a single finger extending in the superior direction at the center of the tip of anterior-posterior alignment member 263. As shown in FIG. 19, when the anterior-posterior alignment members 261, 263 and the central axis of the tibia are aligned and viewed by fluoroscopy, the finger 263A is centered between the fingers 261A, and aligned with the tibia 250. Conversely, when the anterior-posterior alignment members 261, 263 and the central axis of the tibia are not all aligned, the finger 263A is not centered between the fingers 261A, and may not be aligned with the tibia 250. For example, as shown in FIG. 20, the finger 263A may be hidden by one of the fingers 261A, and neither of the medial-lateral alignment members 261, 263 is aligned with the central axis of the tibia 250.

Referring again to FIGS. 17 and 18, a pair of medial-lateral alignment members 260, 262 are inserted through the medial-lateral sleeves 171A, 171B of the anterior-posterior adjustment plate 171. The medial-lateral alignment members 260, 262 are positioned to extend in the superior direction from the anterior-posterior adjustment plate 171. The medial-lateral alignment members 260, 262 are each positioned with the same displacement in the anterior direction from the center of the opening 209 of the foot plate 202. In some embodiments, the medial-lateral alignment members 260, 262 have respective alignment features that are the same as the alignment fingers 261A, 263A of the anterior-posterior adjustment members 261, 263. In some embodiments, the medial-lateral alignment members 260, 262 are attached to a C-shaped arm 267 for ease of handling, and to fix the distance between the members 260, 262. In some embodiments, the arm 267 has another shape, such as a straight bar.

Fixation Procedure

According to some embodiments, a method of positioning a foot includes assembling the foot plate assembly as shown in FIG. 15. The patient's foot is placed onto the assembly 200, with the heel directly over the heel support 208. The heel brackets 220 are adjusted to enclose and support the heel. The forefoot brackets 230 are adjusted to secure the forefoot. The calcaneus is pinned with wires or pins 242, such as 2.4 mm Steinmann Pin, and the wires or pins are cut.

The members (e.g., struts 300) are moved so that a wire or pin 240 (e.g., a 2.4 mm Bayonet tip pin) can be inserted through the eyelets 309 of the guides 308 of each strut 300, and transversely across the midfoot bones. The compression knob 310 of the lateral strut 300 is advanced to move its abutting guide 308 to an inferior position (closer to plate 202) relative to the guide 308 of the medial strut 300. The wire or pin 240 is driven from a superior to inferior direction, through the eyelet 309 of medial strut 300, the bones, and the eyelet 309 of the lateral strut 300. The knobs 306 are then tightened to lock the struts 300 in position against the plate 202. The wire or pin 240 is cut or bent. The compression knobs 310 are then tightened to compress the midfoot to the foot plate 202. The configuration is now as shown in FIG. 16.

The screws 210 are retracted, the heel support 208 is removed, and the foot plate assembly 200 is attached to the ring 164 of the foot holder assembly 100. The opening 209 of the foot plate 202 is placed around the ring 164 of the rotation base plate 173. The screws 210 are advanced enough to retain the foot plate assembly 200 without locking the rotation angle of the assembly 200. The rotational position of the foot plate assembly 200 can be moved to the angle for Mortise view. The configuration is now as shown in FIG. 17.

The tibia 250 is positioned in the support 106 of the joint space stabilizer assembly 104, so the shaft of the tibia is parallel with the base 102 of the foot holder 100. The tibia is rotated so the tibial tubercle is approximately perpendicular to the base plate 102. The tibia is secured to the support 104 by inserting a wire or pin 244 (e.g., a 2.4 mm Bayonet tip pin) through the tibia and through openings 107 on medial and lateral sides of the support 106, as shown in FIG. 18. The wire or pin 244 can be bent to prevent it from backing out.

Once the tibia 250 is secured, the joint space is set by using the knob 112 (to rotate the pinion 114 and position the rack 116 (FIG. 1). This controls the tension of the ligaments and soft tissue of the ankle.

Once the desired tension is achieved, the lock knob 110 can be used to fix the tension. The lock 110 is advanced to lock the position of the rack 116. At this point, the position of the Achilles supports 130 can be adjusted and locked.

Foot Alignment

The Anterior-Posterior alignment members (e.g., rods) 261, 263 are inserted through the socket 168 and opening or cutout 169. In some embodiments, the members 261, 263 are both attached to an arm 265 for ease of handling and to maintain proper spacing and orientation of each member, as shown in FIG. 17.

To obtain a better view of the ankle mortise, the patient's leg is internally rotated just enough so that the lateral malleolus (which is normally posterior to the medial malleolus), is on the same horizontal plane as the medial malleolus.

Usually this involves approximately 10-20 degrees of internal rotation. In other words, when viewing the mortise view, the tibia and fibula are viewed without superimposition on each other. This mortise view represents a true anterior-posterior projection of the ankle mortise and also provides a good visualization of the talar dome.

The apparatus described herein provides internal-external rotation while the foot is fixed by the footholder assembly 100. Internal-External rotation is important in establishing the mortise-view for proper evaluation of the joint congruency and ligamentous balance, and for proper sizing of the prosthesis. Using the apparatus 100 described herein, the mortise view can be determined after the surgeon fixes the foot to the footholder assembly 100. There is no need to unpin the foot prior to changing the rotation angle of the foot, or re-pin the foot after changing the angle. The foot can be placed in and pinned to the foot plate assembly 200, and then footplate assembly 200 is attached to the footholder 100. The mortise view can be established thereafter. The internal-external rotation allows surgeons greater degree of control and minimizes the chances of the foot orientation changing (which could occur when trying to pin the foot in the proper location if the angle of the foot plate could not rotate. Furthermore, in revision surgeries, establishing the mortise view is even more challenging than for a healthy ankle, since the boney anatomy is considerably damaged. The apparatus 100 described herein allows the surgeon to pin the foot in place on the footplate assembly 200 and consider several orientations, without re-pinning the foot every time the surgeon wants to change the internal-external rotation.

The foot plate assembly 200 is rotated about the ring 164, until a fluoroscopic anterior-posterior image of the ankle is as shown in FIG. 19. The finger 263A of member 263 is centered between the fingers 261A of member 261A, and is centered and aligned with the longitudinal axis of the tibia. The medial-lateral adjustment knob 179 (FIG. 5) can be loosened, and the medial-lateral adjustment plate 170 can be moved to align the members 161, 163 with the center of the talus. The U-bracket knobs 147 can be loosened, and the U-shaped bracket 146 can be rotated about an anterior-posterior axis until the anterior-posterior adjustment members 261, 263 are parallel with the central axis of the tibia. If appropriate, translation (of the medial- lateral adjustment plate 170) and rotation (of the U-shaped bracket 146), and fluoroscopic verification can be repeated one or more times. When the correct position of FIG. 19 is achieved, the U-bracket knobs 147 are tightened to fix the position.

FIG. 20 shows an improper alignment for comparison. The finger 263A of member 263 is not centered between the fingers 261A of member 261, and in this image, is hidden behind one of the fingers 261A. The members 261, 253 are not centered along the longitudinal axis of the tibia.

With the anterior-posterior alignment completed, the medial-lateral alignment is checked. When viewed in a lateral fluoroscopic image, the medial-lateral adjustment members 260, 262 should be aligned in the same manner as the anterior-posterior adjustment members 261, 263, as discussed above, with finger 262A between fingers 260A. The joint space between talus and tibia is also checked, and the Achilles support 130 can be adjusted for proper tibia position. The medial-lateral alignment is correct when a fluoroscopic medial-lateral image of the ankle shows the finger 262A of member 262 is centered between the fingers 260A of member 260, and is centered and aligned with the longitudinal axis of the tibia. If the medial-lateral adjustment members 260, 262 are not aligned with or parallel to the central axis of the tibia, the flexion knobs 141 (FIG. 17) can be loosened, and the side plates 152 of the base plate assembly 150 are rotated about the medial-lateral axis 143 (FIG. 3) until the medial-lateral adjustment members 260, 262 are aligned with the central axis of the tibia. Then the flexion knobs 141 are tightened. In some embodiments, a lock is provided to prevent the flexion knobs 141 from loosening inadvertently once they are tightened.

Upon returning to the anterior view, the anterior-posterior alignment is checked again, because it may have shifted during the medial lateral alignment. If appropriate, the anterior-posterior alignment is adjusted. The anterior-posterior alignment should be checked and/or adjusted last.

Figure 21:
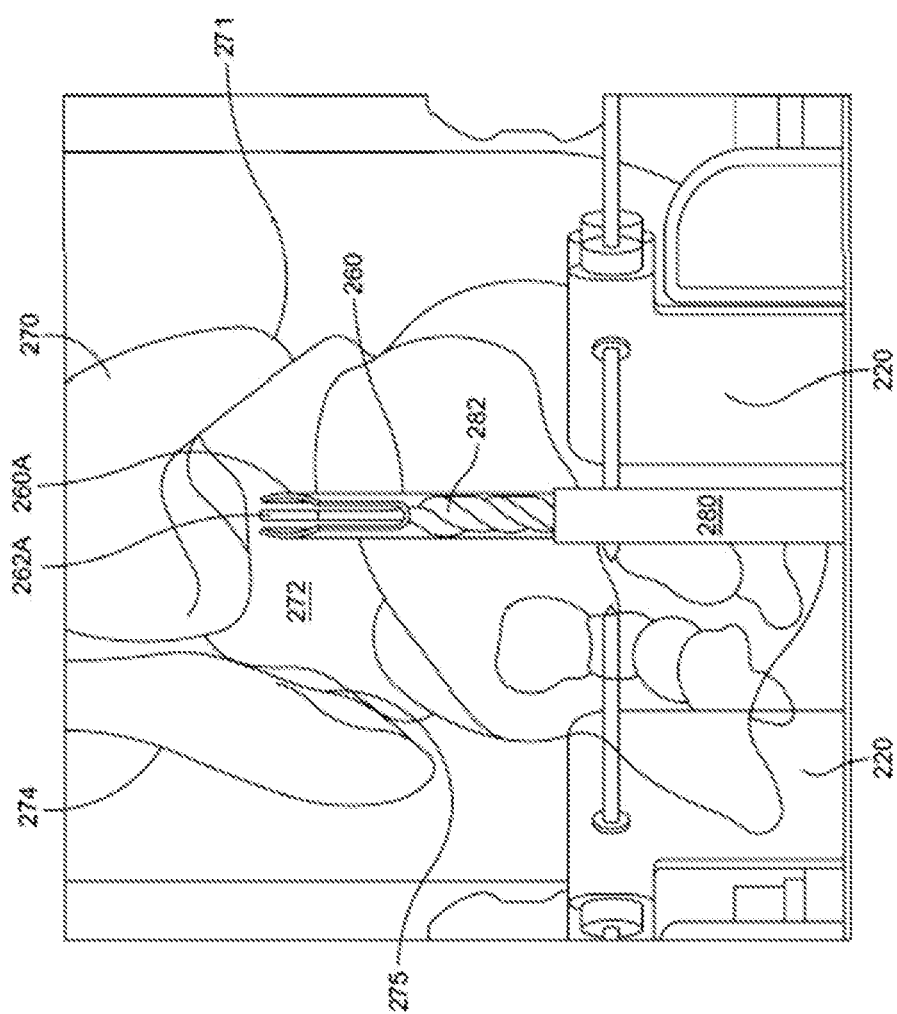
FIG. 21 shows cannula and drill positioned for drilling the primary hole along the axis of the tibia.

A bushing (not shown) is inserted into the port 172 of the medial-lateral adjustment plate 170. A cannula nut and collet (not shown) are inserted into the bushing. The bushing, cannula nut and collet are sized to receive a cannula 280 (FIG. 21) and trocar (not shown). The trocar and cannula 280 are inserted through the soft tissue of the bottom of the foot, until the calcaneus is reached. The cannula nut is then used to lock the cannula 280 in place. The trocar is removed, and the drill bit 282 (FIG. 21) is inserted. The drill bit 282 is used to drill the primary hole through the calcaneus and into the tibia.

Joint Space Cuts

Figure 22:
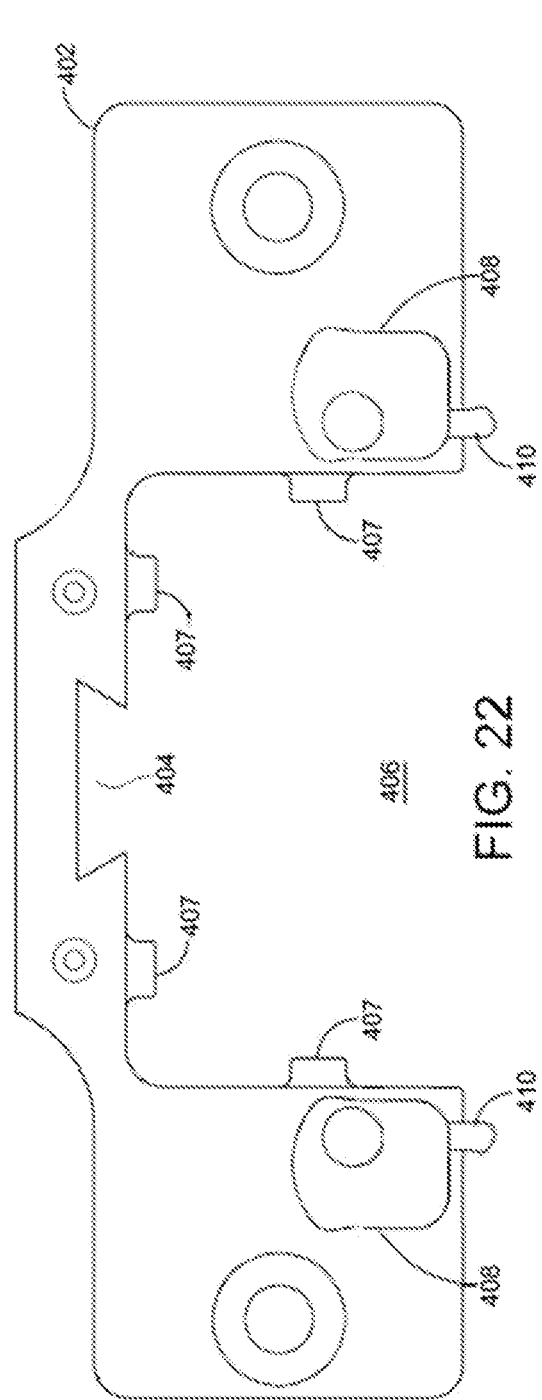
FIG. 22 is a front view of a cartridge holder configured to be attached to an anterior fixture guide that mounts to the anterior side of the foot holder assembly of FIG. 17.

FIG. 22 shows an exemplary embodiment of a resection guide cartridge holder 402. Orthopedic revision joint procedures described herein provide the surgeon with a variety of implants in order to address the variations in the boney defect. The surgeon is provided a large selection of implants and an instrumented technique that allows surgeons to quickly template the boney defect. The resection guide cartridge holder 402 is an instrument that allows surgeons to quickly connect various cut guides and sizing guides when templating the bone.

An anterior fixture guide 401 (shown in FIG. 26) is attached to the side plates 152 of the base plate assembly 150. The anterior fixture guide 401 holds and positions the cartridge holder 402 of FIG. 22. The anterior fixture guide 401 permits the surgeon to adjust a position of the cartridge holder 402 in a superior-inferior direction relative to the talus 272, while the cartridge holder 402 is attached to the foot holder 100. The anterior fixture guide 401 can be the "INBONE®" Anterior Fixture Guide sold by Wright Medical Technology, Inc. of Memphis, Tenn. The Anterior Fixture Guide 401 has adjustments for moving the cartridge holder 402 in the superior/inferior direction, the medial/lateral direction, and/or the anterior/posterior direction, and rotate. For example, in some embodiments the anterior fixture guide 401 has an anterior/posterior adjustment knob 405, a superior/inferior adjustment knob 409, and a medial/lateral lock knob 411. Once the position of the cartridge holder 402 is set, various sizing guides 440 and/or saw guides 420 can be reliably and repeatably positioned in the cartridge holder 402.

FIG. 22 is a front view of a cartridge holder 402 configured to be attached to an anterior fixture guide 401 (FIG. 26) that mounts to the anterior side of the foot holder assembly 100 of FIG. 17. For example, in some embodiments, fasteners 403 attach the cartridge holder 402 to anterior fixture guide 401. Anterior fixture guide 401 can be attached to the base 102 and provides a platform anterior to the base 102 and the calf of the patient, and superior to the surgical site. In some embodiments, the anterior fixture guide 401 can be positioned at a variety of locations along the superior-inferior direction.

Figure 24:
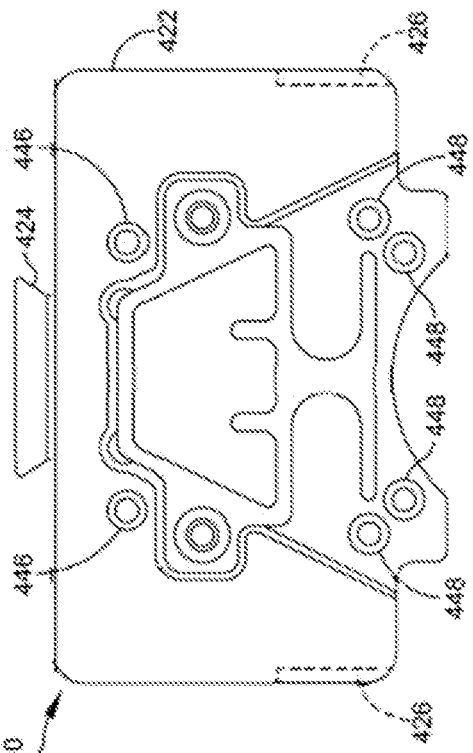
FIG. 24 is a front view of a sizing guide configured to be mounted in the cartridge holder of FIG. 22.

Referring again to FIG. 22, the cartridge holder 402 has an opening 406 to receive either a saw guide (resection guide) 420 (FIG. 23) or a sizing guide 440 (FIG. 24). Once aligned and positioned, the cartridge holder 402 remains in place through both sizing and sawing, to accurately position the holes of the sizing guide 440 relative to the cuts made with the saw guide 420 (and vice-versa). Both the saw guide 420 and sizing guide 440 are sized and shaped to closely fit the opening 406 of the cartridge holder 402.

In some embodiments, multiple features ensure reproducible alignment between the cartridge holder 402 and the saw guide 420 or sizing guide 440. For example, the opening 406, saw guide 420 and sizing guide 440 are generally rectangular, and three sides of the saw guide 420 or sizing guide 440 abut corresponding sides of the opening 406 when the saw guide 420 or sizing guide 440 is in place. The cartridge holder 402 has a plurality of inwardly projecting tabs 407 positioned behind the rear surface of the saw guide 420 or sizing guide 440. The tabs 407 abut the rear surface when the saw guide 420 or sizing guide 440 is properly located in the anterior-posterior direction. In some embodiments, the cartridge holder 402 has a dove-tail opening for receiving a corresponding dove-tail 424 on the saw guide 420 or sizing guide 440. When saw guide 420 or sizing guide 440 is in place, a dove-tail joint is formed, resisting medial-lateral and superior-inferior motion.

In some embodiments, the cartridge holder 402 has a pair of lock knobs 408 having locking tabs 410. The saw guide 420 and sizing guide 440 have corresponding slots 426 on their side edges. When the knobs 408 are turned, the locking tabs 410 extend into the slots 426 to lock the saw guide 420 or sizing guide 440 and prevent any anterior-posterior motion.

Figure 23:
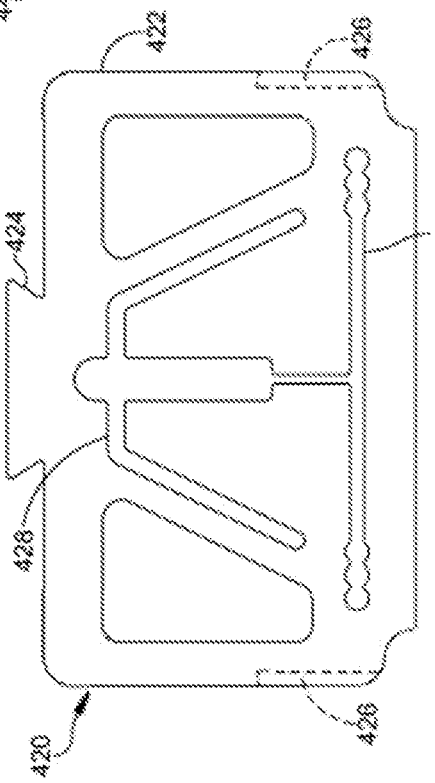
FIG. 23 is a front view of a resection guide configured to be mounted in the cartridge holder of FIG. 22.
Figure 38:
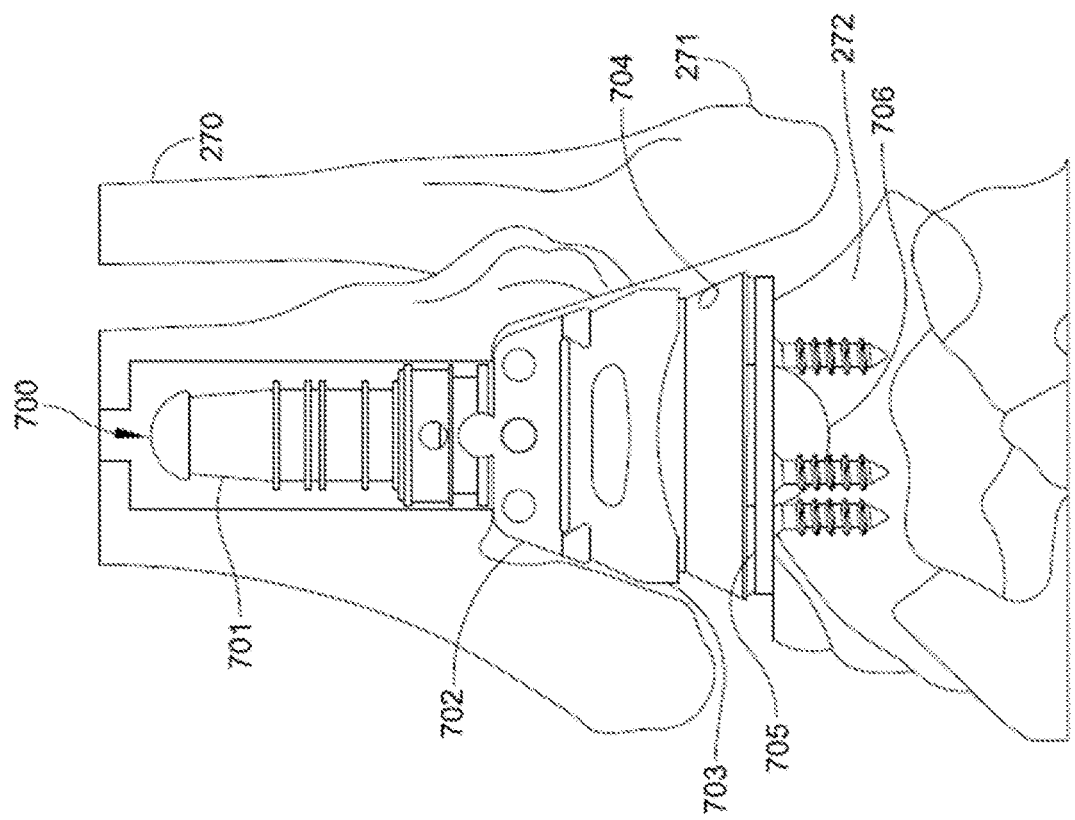
FIG. 38 shows the total ankle replacement after insertion.

FIG. 23 is a front view of an embodiment of a saw guide 420 configured to be mounted in the cartridge holder 402 of FIG. 22. The saw guide 420 has a combination of a tibial slot 428 and a talar slot 430. The surgeon selects an appropriately sized saw guide 420 that will not cut the fibula and preserves much of the medial malleolus. The surgeon performs the appropriate cuts, removes bone from the tibia and talus, and reams the primary hole in the tibia sufficiently to receive the stem 701 of the implant 700 (FIG. 38). The saw guide 420 is removed from the cartridge holder 402, and the sizing guide 440 is attached.

FIG. 24 is a front view of a sizing guide 440 configured to be inserted in the cartridge holder 402 of FIG. 22. The sizing guide 440 ensures correct location of any pins or wires that are used during the ankle replacement surgery.

Figure 25:
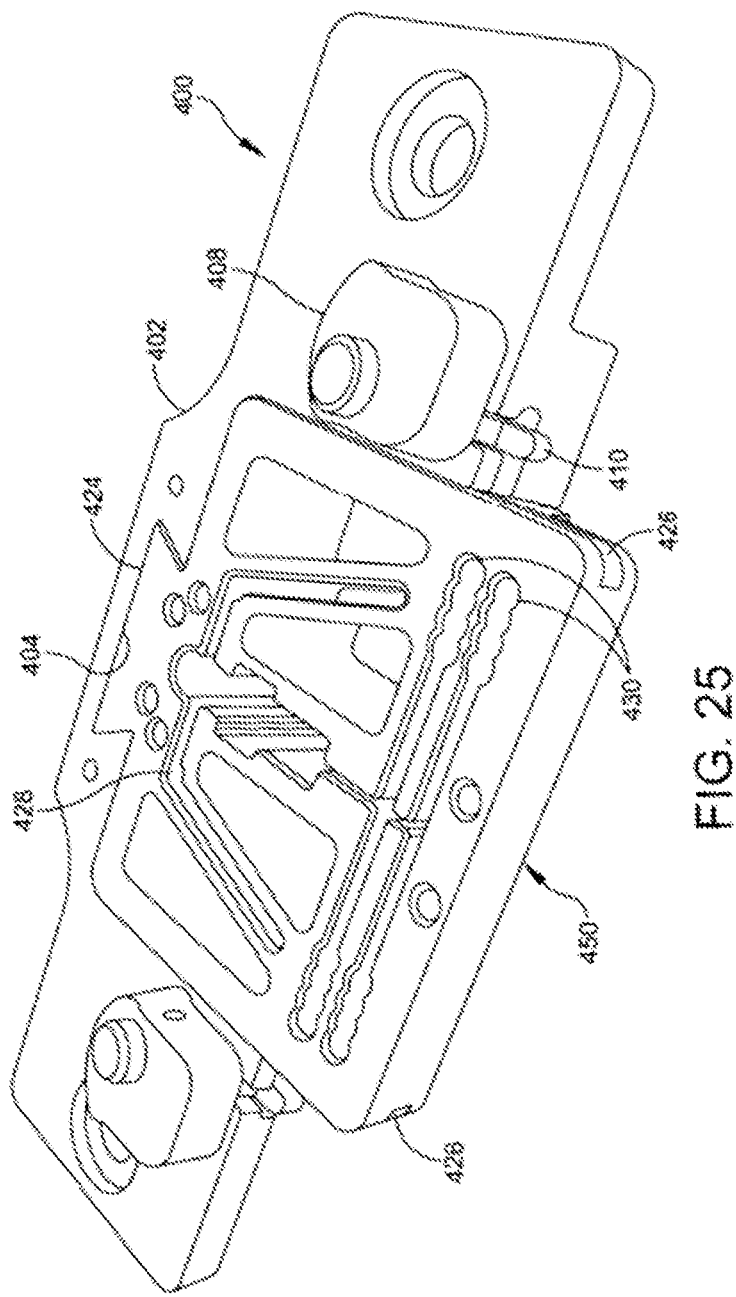
FIG. 25 is an isometric view showing the resection guide of FIG. 23 mounted in the cartridge holder of FIG. 22.
Figure 26:
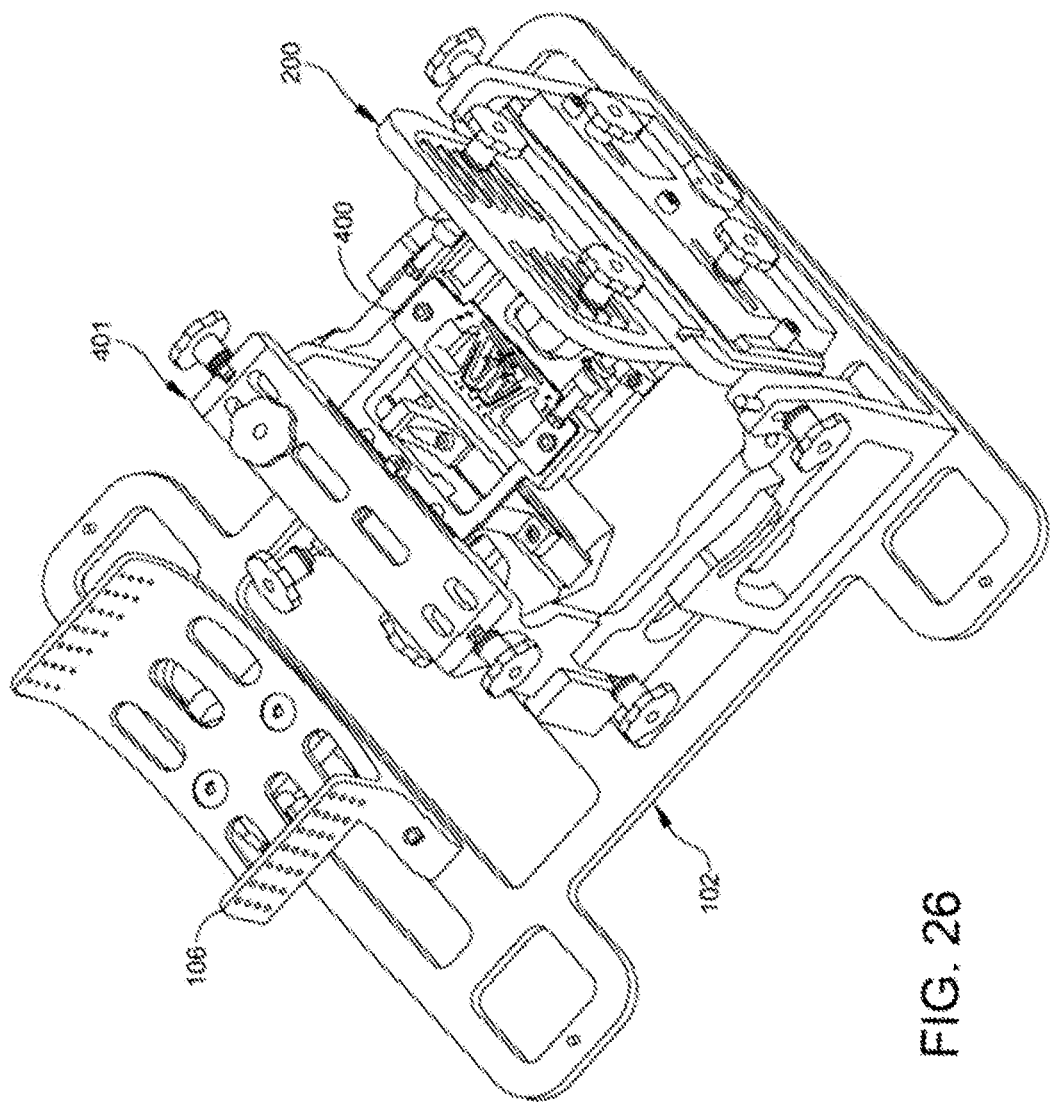
FIG. 26 is an anterior view of the assembly of FIG. 25 mounted on the anterior fixture guide of FIG. 22.

FIG. 25 is an isometric view showing a saw guide mounted in the cartridge holder of FIG. 22. FIG. 26 is an anterior view of the assembly of FIG. 25 mounted on the anterior fixture guide of FIG. 22.

Figure 27:
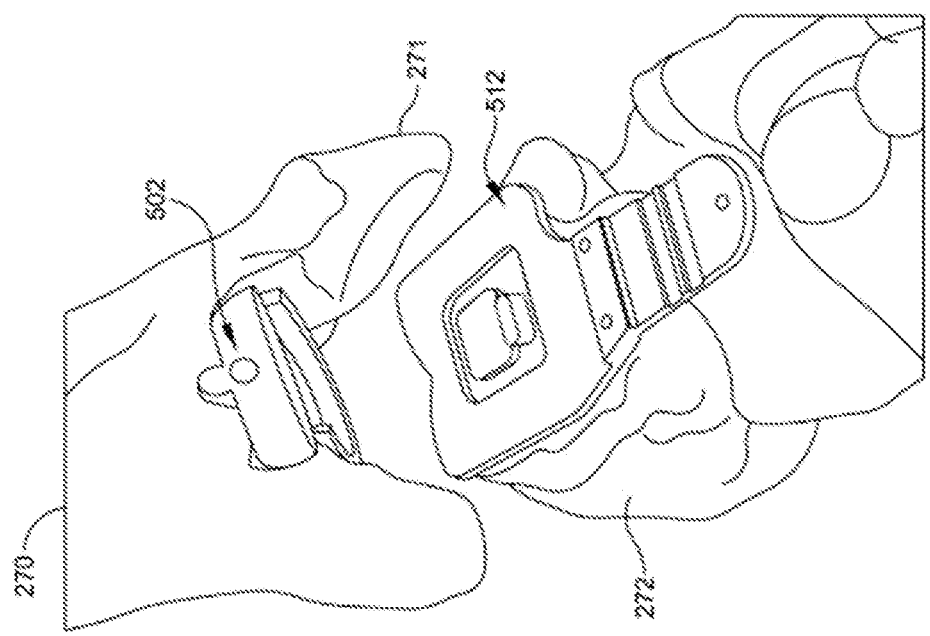
FIG. 27 is an isometric view showing the tibia and talus with the tibia trial with the talar plate trial therein.

FIG. 27 is an isometric view showing the tibia 250 and talus 272 with the tibia trial 502 and the talar plate trial 512 therein. The trials 502, 512 are used for proper sizing and to ensure that the bone surfaces have been cut properly with no bone fragments impeding proper positioning and seating of the tibial support and talar plate.

Figure 28:
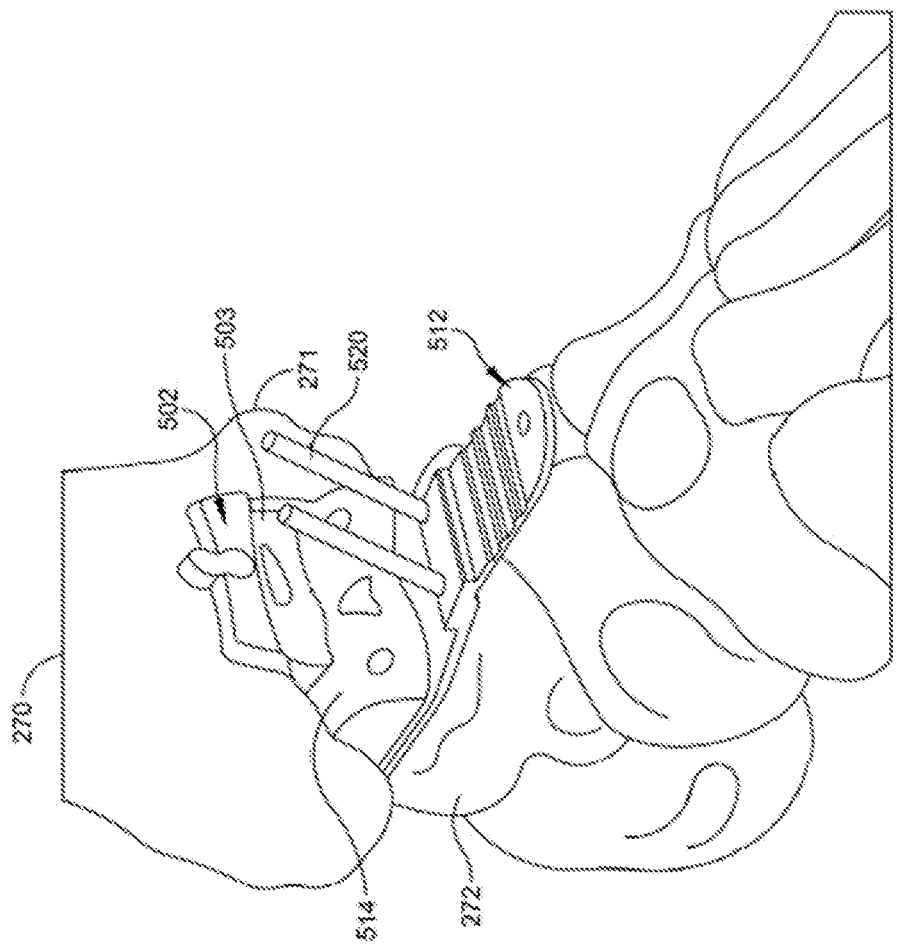
FIG. 28 shows the tibia trial with the poly insert trial and the talar plate trial with the talar dome trial thereon.

FIG. 28 shows the tibia trial 502 with the poly insert trial 503 and the talar plate trial 512 with the talar dome trial 514 thereon. The trials allow verification of proper size and smooth range of motion. Once the surgeon is satisfied with the selection of trials, a pair of wires or pins 520 (e.g., 2.4 mm Steinmann pins) are inserted into the talus 272 through openings in the talar plate trial 512, and the trials 502, 503, 512, 514 are removed.

Augment Reamer

Figure 29:
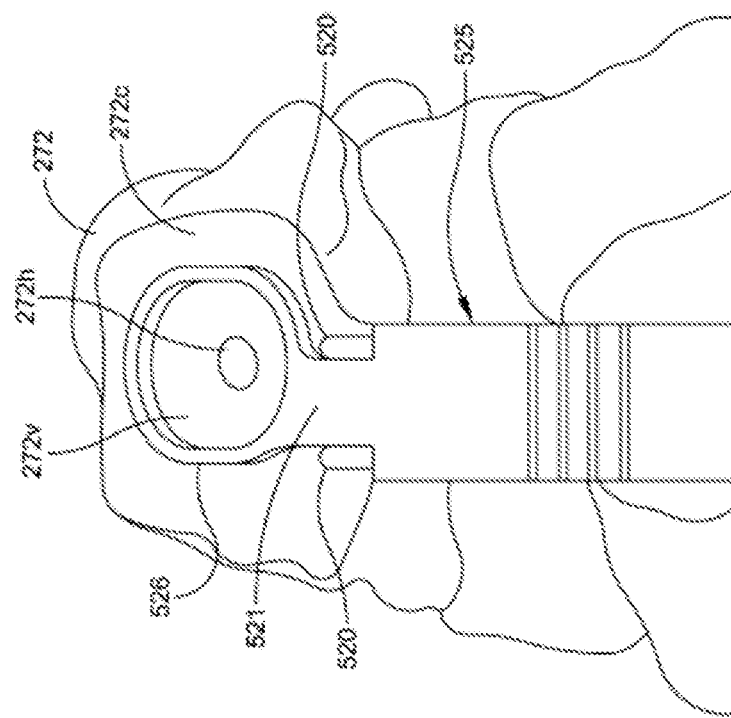
FIG. 29 shows an augment sizer used to determine the optimal augment size for filling a void in the talus.

If the talus 272 has a pre-existing bone defect, such as a void 272v FIG. 29, a talar plate 705 (FIG. 38) having an augment 706 can be used to fill the void 272v. Some embodiments of this disclosure provide tooling for reaming the void 272v to a predetermined size and shape to receive an augment of a predetermined size and shape.

The surgeon utilizes an array of lolli-pop templates that define the shape and position of the talar defect. For example, in some embodiments, templates are provided in two different shapes, central and oblong, and two different depths, 6 mm and 10 mm. The surgeon templates the boney defect by referencing the augment sizer against the two angled pins 520 positioned at the neck of the talus 272 from the talar trial or talar sizer. Once the appropriate template is identified the surgeon will outline the defect based on the template.

FIG. 29 shows a lolli-pop style augment sizer 525 used to determine the optimal augment size for filling a void in the talus 272. In some embodiments, the augment sizer 525 has a neck 521 having a width that matches the distance between the pins 520. In the exemplary embodiment of FIG. 29, the augment selection is made with reference to the pins 520, and not necessarily with reference to the primary talar hole 272h. In other embodiments (not shown), the augment sizer 525 has a pair of holes sized and positioned to receive the pins 520. In other embodiments, once the augment reamer base 600 is slid onto the pins 520, the arm 604 is adjusted till an axis of rotation of the reamer 630 is aligned with the previously drilled hole 272h in the talus 272. The surgeon tries a plurality of augment sizers 525, and selects the one for which the least reshaping will be performed (thus preserving the maximum amount of bone). Once the augment size is determined, the void is reshaped, using the reamer base 600 and reamer 630, as shown in FIGS. 30-37. Additionally, the void can be reshaped using other operating room tools, such as, but not limited to, burrs, curettes, or the like.

Figure 30:
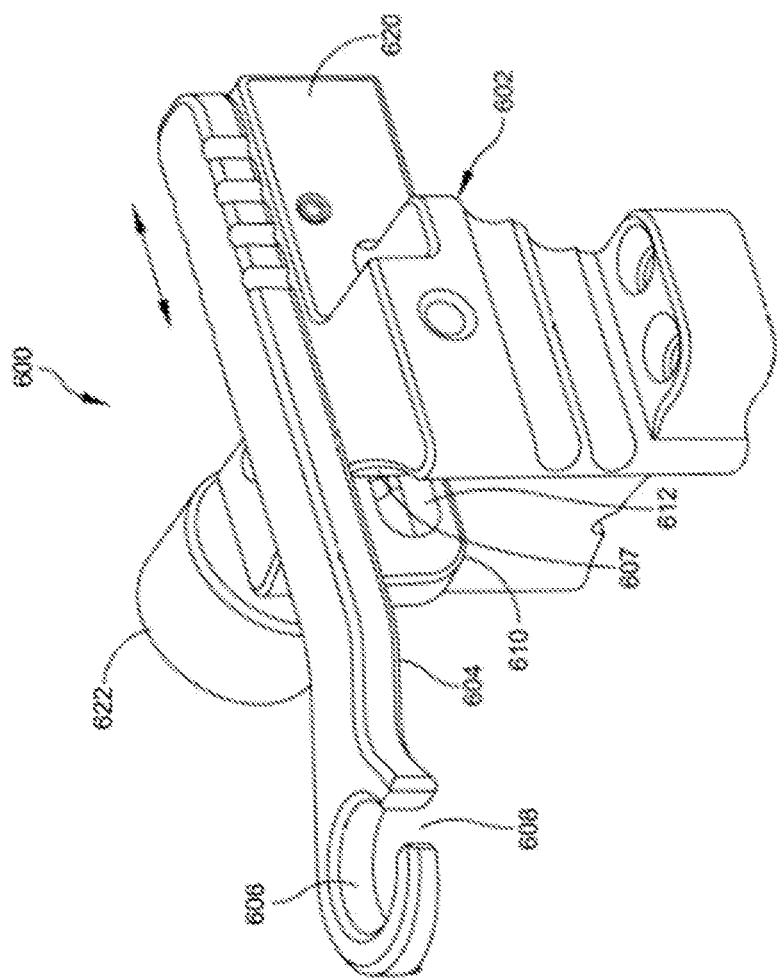
FIG. 30 is an isometric view of an augment reamer base for positioning and aligning an augment reamer for enlarging the void in the talus to receive a predetermined augment.

FIG. 30 is an isometric view of an augment reamer base 600 for positioning and aligning an augment reamer 630 for enlarging the void 272v in the talus 272 to receive a predetermined augment 706. The reamer base 600 is used after: cutting the talus 272 along a transverse plane to form a cut surface of the talus, wherein the talus has a void 272v in the cut surface, the void having a size and a location; fitting a talar trial component 512 to the cut surface of the talus 272; inserting a plurality of wires or pins 520 through the talar trial component 520 into the talus; and removing the talar trial component 512.

The reamer base 600 has an adjustably positionable arm 604 for positioning the reamer 630. The arm has a circular opening 606 with a cutout 608. The arm 604 is movable in the anterior-posterior direction. In some embodiments, the arm 604 is attached to a rail 620, which is slidably mounted in a groove 607 in the reamer base body 602. The rail 620 has a slot 612, through which a locking screw 622 passes. When the locking screw 622 is tightened, a bearing surface (not shown) of locking screw 622 applies a force against the slide 610, locking the position of the arm 604. In some embodiments, each talar plate/augment configuration has a respective predetermined anterior-posterior position of the arm 604 with respect to the body 602 of the augment reamer base 600.

Figure 31:
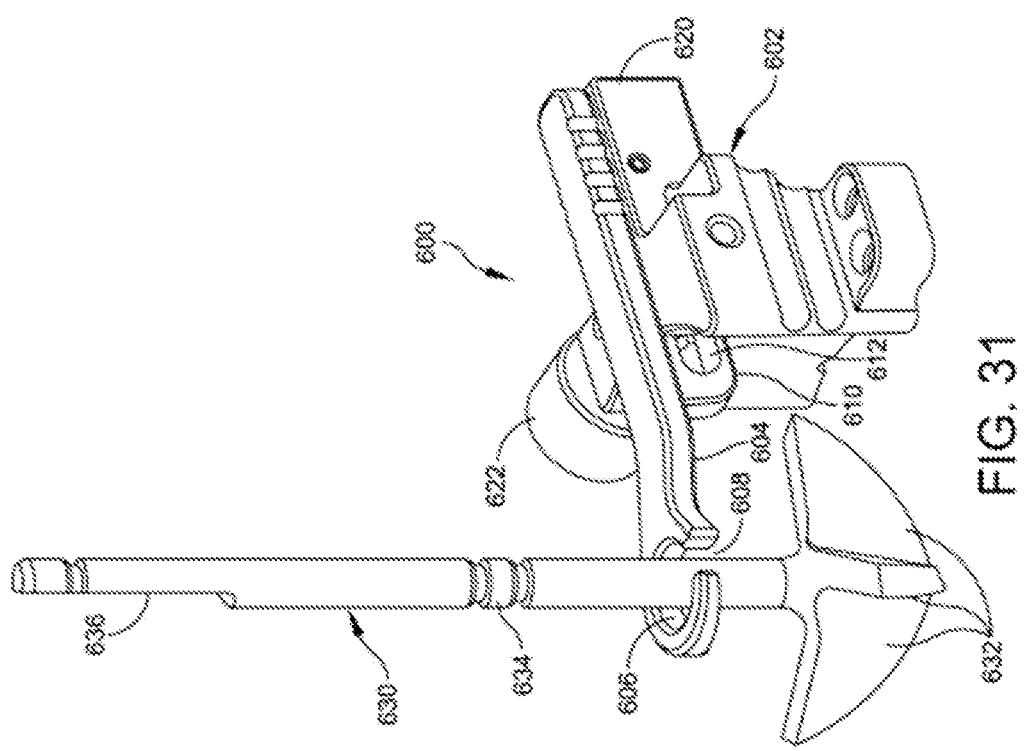
FIG. 31 shows a reamer inserted into the arm of the augment reamer base of FIG. 30.
Figure 34:
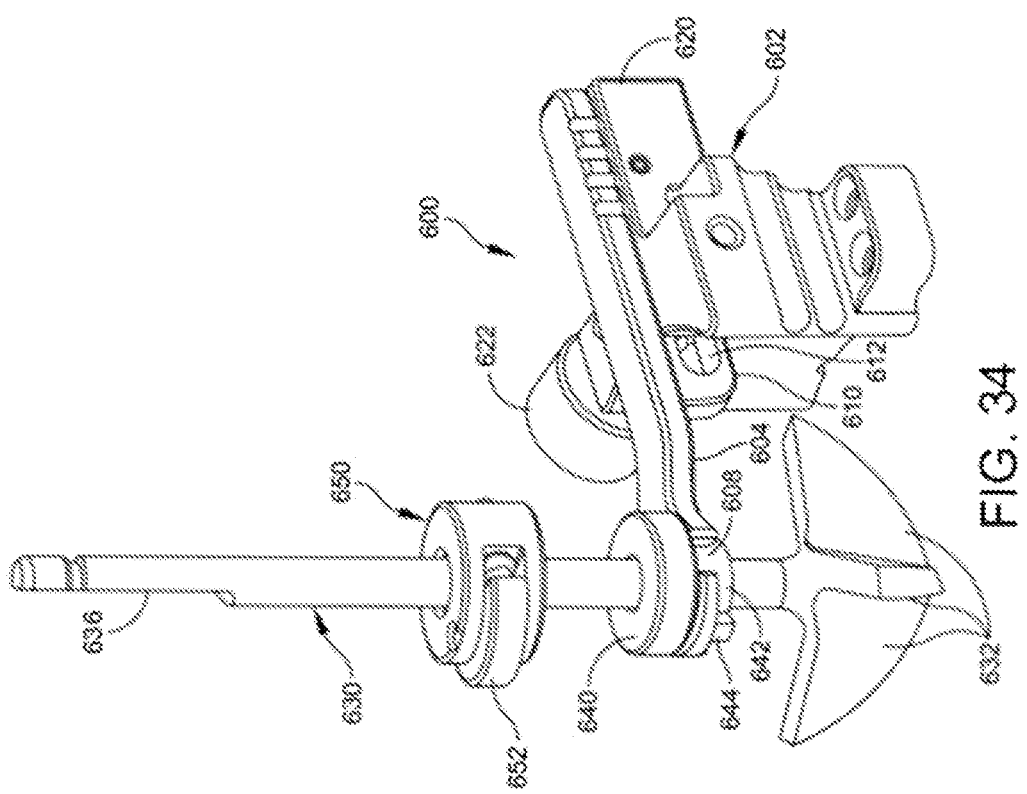
FIG. 34 shows the augment reamer base of FIG. 33 with a stop positioned above the collar.
Figure 36:
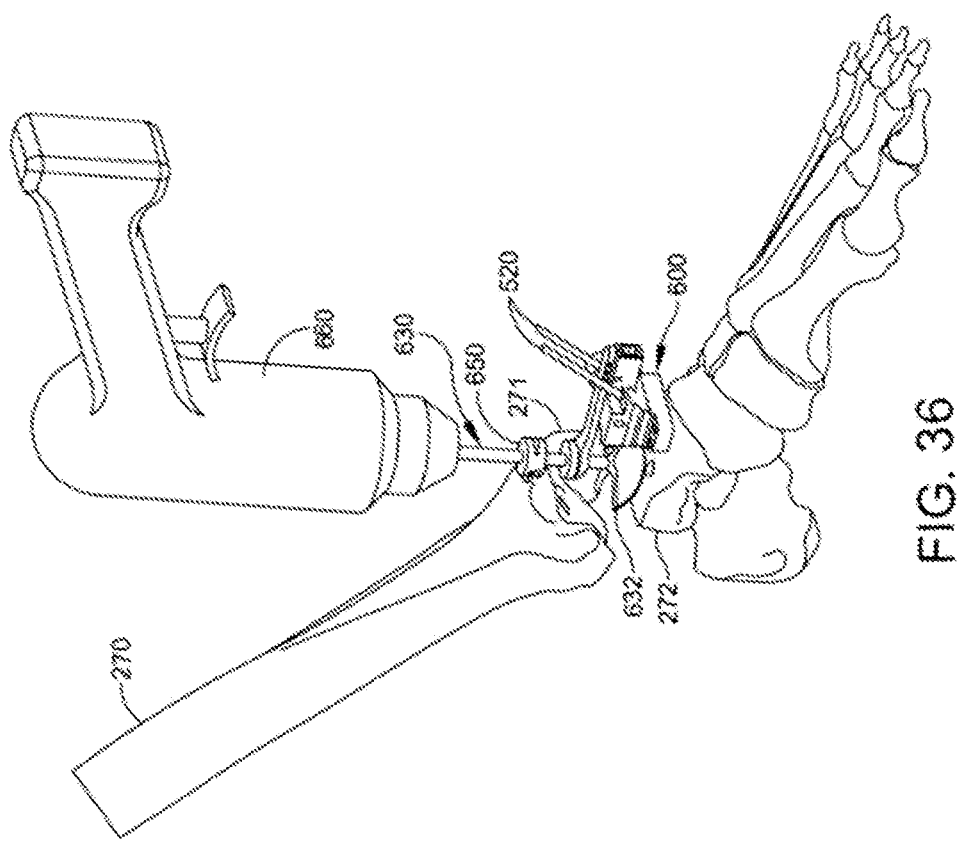
FIG. 36 shows the augment reamer base of FIG. 35 with a drill attached to the reamer.

FIG. 31 shows a reamer 630 inserted into the opening 606 of the arm of the augment reamer base 600. The reamer 630 has one or more blades 632 corresponding to the augment 706 that will be installed in the talus 272. The reamer 630 has a means for limiting an advance of the reamer to a predetermined distance. In some embodiments, the means for limiting include an adjustable stop 650. The reamer 630 has a feature (e.g., ridge) 634 for attaching a stop 650 (FIG. 34). The reamer 630 also has a proximal end 636 configured for mounting in the chuck of a drill 660 (FIG. 36). Although FIG. 31 shows a D-shaped end 636, a variety of shapes can be used to accommodate the chuck of the drill to be used.

Figure 32:
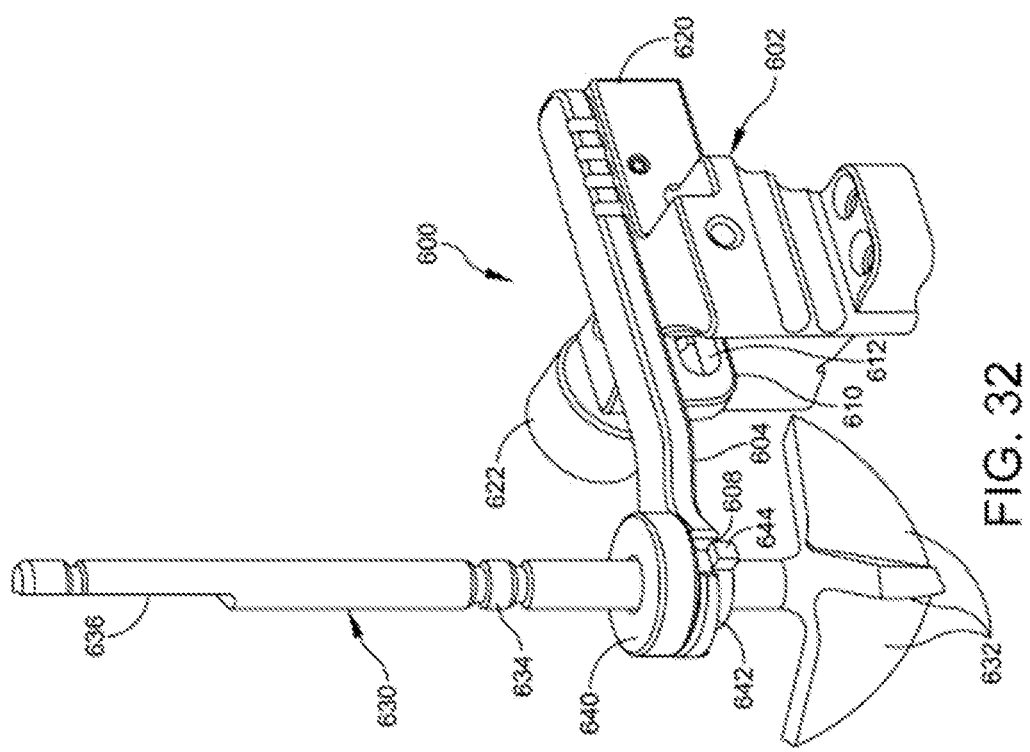
FIG. 32 shows the augment reamer base of FIG. 31 with a collar inserted in the arm.

FIG. 32 shows the augment reamer base of FIG. 31 with a collar 640 inserted in the circular opening 606 of the arm 604. The collar 640 has a smooth circular inner diameter, configured to position and align the reamer 630, while permitting the reamer to rotate freely. The collar 640 has an outer diameter 642 sized to fit within the circular opening 606. A set of collars 640 can include respectively different inner diameters (for respectively different reamers 630), but the same outer diameter 642, sized to fit the opening 606. The collar 640 has a locking member 644 sized to fit the cutout 608 of the circular opening 606.

Figure 33:
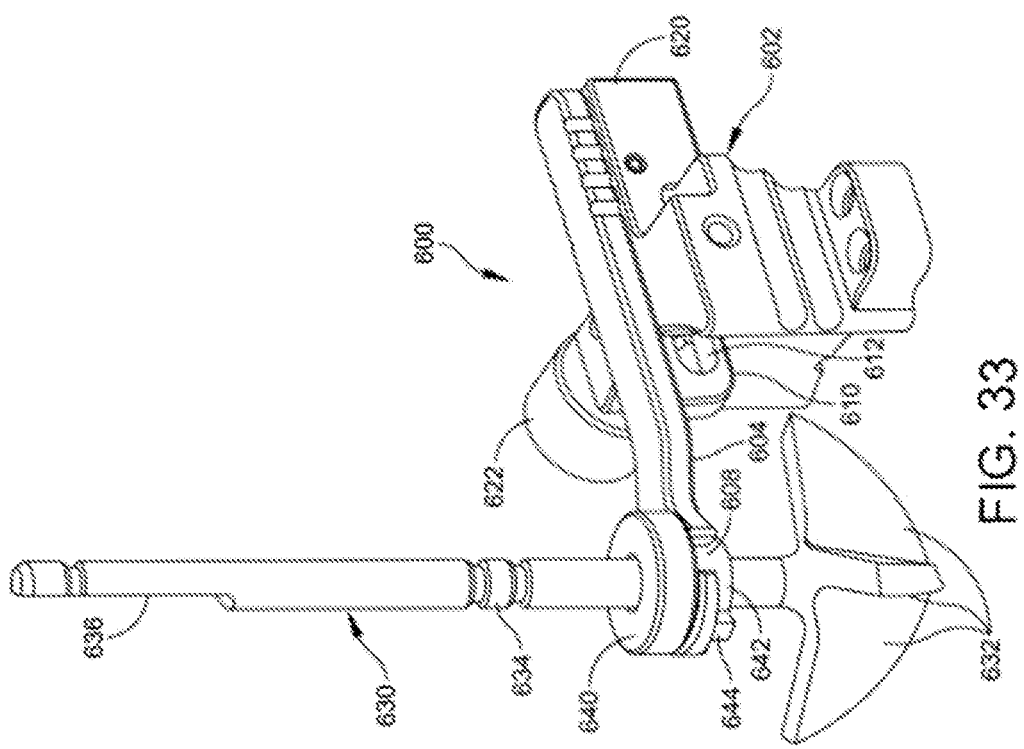
FIG. 33 shows the augment reamer base of FIG. 32 with the collar in a locked position.

FIG. 33 shows the augment reamer base of FIG. 32 with the collar 640 rotated so the locking member 644 is in a locked position. This prevents the collar from being inadvertently removed from the arm 604.

FIG. 34 shows the augment reamer base of FIG. 33 with a stop 650 positioned above the collar 640. The stop 650 can have a variety of configurations. For example, in the example of FIG. 34, the stop 650 has a spring loaded member (not shown) which is biased to a locking position when no external force is applied to the release 652. When the release 652 is pressed inwardly, the spring loaded member releases the ridge 634, so the stop 650 can be removed.

Figure 35:
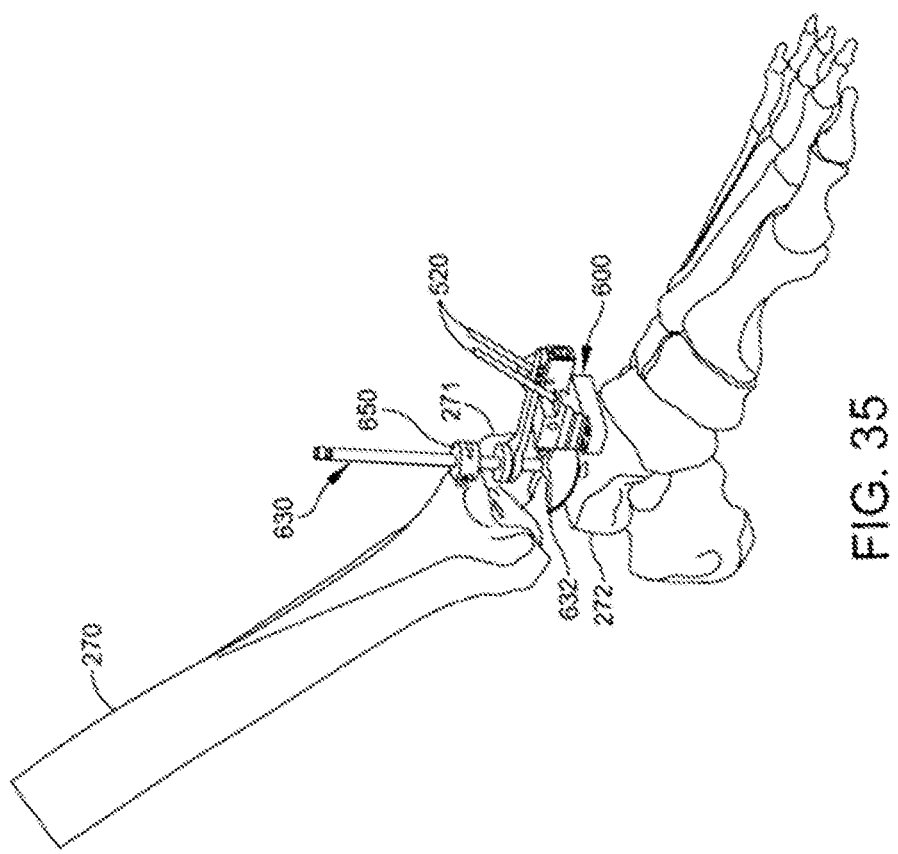
FIG. 35 shows the augment reamer base of FIG. 33 in position at the surgical site.

FIG. 35 shows the augment reamer base 600 of FIG. 34 in position at the surgical site. The body 602 of the augment reamer base 600 has two diagonal holes configured to fit over the pins 520, which were previously inserted at the conclusion of talar plate trialing. Sliding the holes in the body 602 of augment reamer base 600 over the pins 520 accurately locates the augment reamer base 600 relative to the location at which the talar plate 705 is to be attached. A supplementary threaded pin (not shown) can be placed at an oblique angle to provide greater stability to the instrument.

FIG. 36 shows the augment reamer base 600 of FIG. 35 with a drill 660 attached to the reamer 630. The surgeon activates the drill 660, and reams the talus until the stop 650 abuts the collar 640.

Figure 37:
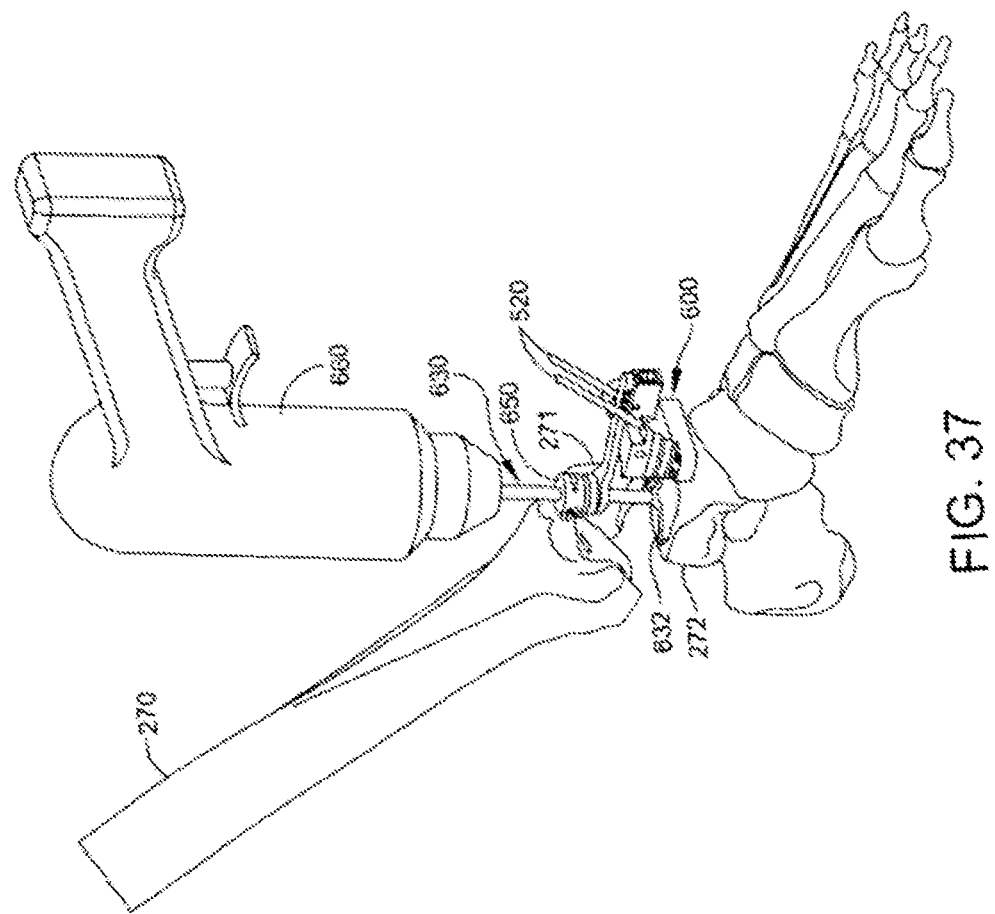
FIG. 37 shows the augment reamer base of FIG. 36 after the reamer has advanced a predetermined distance, so the stop abuts the collar.

FIG. 37 shows the augment reamer base of FIG. 36 after the reamer has advanced to a predetermined height, so the stop abuts the collar. The ridge 634 and stop 650 are configured to provide a predetermined distance between the bottom of the stop 650 and the bottom of the reshaped void 272v when the stop 650 abuts the collar 640. Because the ridge 634 locates the stop 650 at a predetermined distance from the bottom of the reamer blades 632, proper functioning of the reamer 630 is not sensitive to the initial distance between the stop 650 and the collar 640. Rather, a first distance from the bottom of the stop 650 to the bottom of the blades 632 corresponds to a second distance between the bottom of the talar plate 705 and bottom of the augment 706. (The first distance and second distance can differ from each other by a constant, which depends on the height of the arm 604 above the cut surface of the talus 272.). For example, the second distance between the bottom of the talar plate 705 and bottom of the augment 706 can be 6 mm or 10 mm in some embodiments.

If the void 272v is circular, and the augment 706 is circular, then a single reaming pass prepares the void for the augment. For oblong augments, the reamer 630 can be translated in the anterior-to posterior direction to achieve the proper boney preparation. To translate the reamer 630, the knob 622 is loosened, the arm 604 is advanced or retracted, and the knob 622 is again tightened. The reaming and repositioning can be repeated one or more times to achieve the desired void configuration to receive the augment 706.

FIG. 38 shows the total ankle replacement 700 after insertion. The void 272h has been reshaped to accept the augment 706 of the talar plate 705, with minimal void remaining between the augment 706 and bone. The talar dome 704 of the talar component is mounted on the talar plate 705. The tibial component includes a stem 701 embedded in the tibia, with a tibia tray 702 attached thereto. The tibia tray 702 holds the polyethylene implant 703. The total angle replacement 700 allows a wide range of articulating motion between the polyethylene implant 703 and the talar dome 704. The ankle revision system of FIG. 38 is exemplary, and is not limiting. The apparatus described herein can be used with other types of ankle revision systems, such as a pegged plate revision system, for example.

Although the subject matter has been described in terms of exemplary embodiments, it is not limited thereto. Rather, the appended claims should be construed broadly, to include other variants and embodiments, which may be made by those skilled in the art.

What is claimed is:

1. A method, comprising:
fixing a talus of a patient to a foot holder having a rotation base plate including a retaining body defining a groove so that at least one locking pin is positionable within the groove to prevent translation of the foot holder relative to the retaining body, but permit rotation of the foot holder relative to the retaining body;
aligning the talus with a tibia of the patient;
attaching a cartridge holder to the foot holder;
attaching a resection guide or a sizing guide to the cartridge holder, the cartridge holder and the resection guide or sizing guide configured so that, when the resection guide or sizing guide is attached, the resection guide is positioned and aligned to cut the talus and tibia, or the sizing guide is positioned and aligned to drill holes in the talus and tibia, respectively.

2. A method, comprising:
fixing a talus of a person to a foot holder having a rotation base plate including a retaining body defining a groove so that at least one locking pin is positionable within the groove to prevent translation of the foot holder relative to the retaining body, but permit rotation of the foot holder relative to the retaining body;
aligning the talus with a tibia of the person;
attaching a cartridge holder to the foot holder;
attaching a resection guide or a sizing guide to the cartridge holder, the cartridge holder and the resection guide or sizing guide configured so that, when the resection guide or sizing guide is attached, the resection guide is positioned and aligned to cut the talus and tibia, or the sizing guide is positioned and aligned to drill holes in the talus and tibia, respectively;
implanting a talar component in the talus of the person; and
implanting a tibial component in the tibia of the person, the tibial component configured for articulating motion relative to the talar component.

3. The method of claim 2, wherein the cartridge holder has a plurality of movable tabs, and the step of attaching the resection guide or sizing guide includes:
placing the resection guide or sizing guide in the cartridge holder; and
moving the tabs to extend into respective slots in the resection guide or sizing guide.

4. The method of claim 2, wherein the cartridge holder has a pair of knobs with movable tabs attached thereto, and the step of attaching the resection guide or sizing guide includes:
placing the resection guide or sizing guide in the cartridge holder; and
rotating the knobs, so as to extend the tabs into respective slots in the resection guide or sizing guide.

5. The method of claim 2, further comprising adjusting a position of the cartridge holder in a superior-inferior direction relative to the talus, while the cartridge holder is attached to the foot holder.

6. A method, comprising:
fixing a talus of a person to a foot holder having a rotation base plate including a retaining body defining a groove so that at least one locking pin is positionable within the groove to prevent translation of the foot holder relative to the retaining body, but permit rotation of the foot holder relative to the retaining body;
aligning the talus with a tibia of the person;
attaching a cartridge holder to the foot holder, the cartridge holder having a plurality of movable tabs;
attaching a resection guide or a sizing guide to the cartridge holder, the cartridge holder and the resection guide or sizing guide configured so that, when the resection guide or sizing guide is attached, the resection guide is positioned and aligned to cut the talus and tibia, or the sizing guide is positioned and aligned to drill holes in the talus and tibia, respectively;
implanting a talar component in the talus of the person; and
implanting a tibial component in the tibia of the person, the tibial component configured for articulating motion relative to the talar component.

7. The method of claim 6, wherein the step of attaching the resection guide or sizing guide includes:
placing the resection guide or sizing guide in the cartridge holder; and
moving the tabs to extend into respective slots in the resection guide or sizing guide.

8. The method of claim 6, further comprising adjusting a position of the cartridge holder in a superior-inferior direction relative to the talus, while the cartridge holder is attached to the foot holder.

9. A device, comprising:
a base including a rotation plate with a circular retaining body defining a groove on a side edge thereof;
a foot plate attached to the base, the foot plate having a plurality of members attached thereto, the members configured for receiving at least a first wire or pin to fix a foot of a person relative to the foot plate while the foot plate is oriented normal to a superior-inferior direction of the foot wherein the foot plate has at least one locking pin that is positionable within the groove to prevent translation of the foot plate relative to the retaining body, but permit rotation of the foot plate relative to the retaining body;
an assembly attached to the base, the assembly including:
a support shaped to receive a calf of a person, the support including a medial wall and a lateral wall, the medial and lateral walls configured for attachment of a second wire or pin to fix a tibia of the person in the superior-inferior direction relative to the support; and
a positioning assembly for attaching the support to the base, the support including a rack and a pinion for positioning the rack on the support in a superior-inferior direction relative to the base.

10. The device of claim 9, wherein the positioning assembly further comprises a lock configured to fix a position of the rack in the superior-inferior direction.

11. The device of claim 9, wherein the positioning assembly includes a second mechanism for positioning the support in an anterior-posterior direction perpendicular to the superior-inferior direction.

12. The device of claim 9, including a body attached to the pinion, the body slidable within the groove relative to the base, the channel having a longitudinal axis oriented in an anterior-posterior direction perpendicular to the superior-inferior direction.

13. The device of claim 9, wherein the plurality of members include a plurality of struts that are independently positionable for urging the first wire or pin in an inferior and/or anterior direction relative to the foot plate.

14. The device of claim 13, wherein the plurality of struts each include:
a head configured to slide along a respective anterior-posterior track in the foot plate,
a lock for fixing the location of the strut along the track thereof,
a guide for receiving the wire or pin, the guide slidable along the strut for controlling a position of the wire or pin in the superior-inferior direction, and
a compression knob for advancing the guide in the inferior direction.

15. Apparatus, comprising:
a fixation device, comprising:
a base including a rotation plate with a circular retaining body;
a support attached to the base, the support shaped to receive a calf of a person and adapted to receive a wire or pin for securing a tibia of a person; and
a foot plate attachable to the base and configured to have an axis of rotation aligned with the tibia while the foot plate is attached to the base and the tibia is secured to the support, the foot plate having a plurality of members attached thereto, the members configured for receiving at least a first wire or pin to fix a foot of the person relative to the foot plate while the foot plate is oriented normal to a superior-inferior direction of the foot, the foot plate being rotatable relative to the rotation plate of the base while the foot plate is attached to the base; and
an implant comprising:
a talar component configured to be attached to a talus of the person while the foot is fixed relative to the foot plate; and
a tibial component configured to be attached to a tibia of the person while the calf is fixed by the wire or pin, the tibial component configured for articulating motion relative to the talar component wherein the retaining body has a groove on a side edge thereof, and the foot plate has at least one locking pin that is positionable within the groove to prevent translation of the foot plate relative to the retaining body, but permit rotation of the foot plate relative to the retaining body.

16. Apparatus, comprising:
a fixation device, comprising:
a base including a rotation plate with a circular retaining body;
a support attached to the base, the support shaped to receive a calf of a person and adapted to receive a wire or pin for securing a tibia of a person; and
a foot plate attachable to the base and configured to have an axis of rotation aligned with the tibia while the foot plate is attached to the base and the tibia is secured to the support, the foot plate having a plurality of members attached thereto, the members configured for receiving at least a first wire or pin to fix a foot of the person relative to the foot plate while the foot plate is oriented normal to a superior-inferior direction of the foot, the foot plate being rotatable relative to the rotation plate of the base while the foot plate is attached to the base; and an implant comprising:
- a talar component configured to be attached to a talus of the person while the foot is fixed relative to the foot plate; and
- a tibial component configured to be attached to a tibia of the person while the calf is fixed by the wire or pin, the tibial component configured for articulating motion relative to the talar component wherein the rotation plate has a port for receiving a cannula, and a position of the port is adjustable in the anterior-posterior direction relative to the base.

* * * * *